(12) United States Patent
Vogt et al.

(10) Patent No.: US 11,865,006 B2
(45) Date of Patent: Jan. 9, 2024

(54) DEVICE AND METHOD FOR PRODUCING SPACERS

(71) Applicant: Heraeus Medical GmbH, Wehrheim (DE)

(72) Inventors: Sebastian Vogt, Wehrheim (DE); Thomas Kluge, Wehrheim (DE)

(73) Assignee: Heraeus Medical GmbH, Wehrheim (DE)

( * ) Notice: Subject to any disclaimer, the term of this patent is extended or adjusted under 35 U.S.C. 154(b) by 61 days.

(21) Appl. No.: 17/382,958

(22) Filed: Jul. 22, 2021

(65) Prior Publication Data
US 2022/0047391 A1 Feb. 17, 2022

(30) Foreign Application Priority Data
Aug. 17, 2020 (EP) ...................................... 20191372

(51) Int. Cl.
*A61F 2/00* (2006.01)
*A61F 2/30* (2006.01)
(Continued)

(52) U.S. Cl.
CPC ...... *A61F 2/30724* (2013.01); *A61F 2/30942* (2013.01); *A61F 2/4684* (2013.01);
(Continued)

(58) Field of Classification Search
CPC .......................... A61F 2/30724; A61F 2/30942
See application file for complete search history.

(56) References Cited

U.S. PATENT DOCUMENTS 5,425,768 A * 6/1995 Carpenter ........... A61F 2/30724
623/23.48
5,681,289 A 10/1997 Wilcox et al.
(Continued)

FOREIGN PATENT DOCUMENTS

DE 102015104704 B4 10/2016
EP 2522310 A1 11/2012
(Continued)

OTHER PUBLICATIONS

Search report dated Feb. 3, 2021 by the European Patent Office for priority European patent application no. 20191372.0.

*Primary Examiner* — Nicholas R Krasnow
(74) *Attorney, Agent, or Firm* — Dicke, Billig & Czaja, PLLC

(57) ABSTRACT

The invention relates to a device for producing a spacer having
a stem mold (1) which has an inner space (2), wherein the inner space (2) is accessible via a proximal opening (3) and wherein the stem mold (1) has a proximal wall (4) which peripherally delimits the proximal opening (3) of the stem mold (1),
a head mold (5) which has in the interior thereof a hollow space (6), wherein the hollow space (6) has a spherical surface-shaped inner surface (7) and is accessible via a distal opening (8), wherein the head mold (5) has a distal wall (9) which peripherally delimits the distal opening (8) of the head mold (5),
a metal core (10) which has a stem part (12), a head part (14) and a flange (16), wherein the flange (16) projects out from the metal core (10), is arranged between the stem part (12) and the head part (14) and has a proximal surface (18) and a distal surface (20),
wherein the stem mold (1) and the stem part (12) are shaped such that the stem part (12) is arranged in the
(Continued)

inner space (2), when the proximal wall (4) is resting against the distal surface (20), and wherein the head mold (5) and the head part (14) are shaped such that the head part (14) is arranged in the hollow space (6), when the distal wall (9) is resting against the proximal surface (18).

The invention also relates to a set with such a device and to a method for producing spacers with such a device.

21 Claims, 25 Drawing Sheets

(51) Int. Cl.
| | | |
|---|---|---|
| *A61F 2/46* | (2006.01) | |
| *B29B 7/90* | (2006.01) | |
| *B29C 45/34* | (2006.01) | |
| *B29C 45/36* | (2006.01) | |
| *A61F 2/36* | (2006.01) | |
| *A61F 2/40* | (2006.01) | |
| *B29K 103/08* | (2006.01) | |
| *B29L 31/00* | (2006.01) | |

(52) U.S. Cl.
CPC ............ *B29B 7/90* (2013.01); *B29C 45/34* (2013.01); *B29C 45/36* (2013.01); *A61F 2002/30957* (2013.01); *A61F 2002/3611* (2013.01); *A61F 2002/4018* (2013.01); *B29K 2103/08* (2013.01); *B29K 2905/00* (2013.01); *B29L 2031/7532* (2013.01)

(56) References Cited

U.S. PATENT DOCUMENTS

| | | | |
|---|---|---|---|
| 6,245,111 B1 * | 6/2001 | Shaffner | A61F 2/36 623/22.4 |
| 6,361,731 B1 * | 3/2002 | Smith | B29C 33/405 264/318 |
| 7,637,729 B2 | 12/2009 | Hartman et al. | |
| 7,789,646 B2 | 9/2010 | Haney et al. | |
| 8,480,389 B2 | 7/2013 | Haney et al. | |
| 8,801,983 B2 | 8/2014 | Haney et al. | |
| 8,900,322 B2 | 12/2014 | De Beaubien | |
| 2007/0222114 A1 | 9/2007 | Ziran et al. | |
| 2009/0157189 A1 * | 6/2009 | Hartman | B28B 1/24 606/92 |
| 2010/0042213 A1 | 2/2010 | Nebosky et al. | |
| 2011/0015754 A1 | 1/2011 | Eonard et al. | |
| 2019/0290833 A1 * | 9/2019 | Vogt | A61F 2/36 |

FOREIGN PATENT DOCUMENTS

| | | |
|---|---|---|
| EP | 2617393 B1 | 7/2015 |
| EP | 1991170 B1 | 10/2016 |
| EP | 2787928 B1 | 7/2017 |
| WO | 2009073781 A2 | 6/2009 |
| WO | 2016205077 A1 | 12/2016 |
| WO | 2017178951 A1 | 10/2017 |

* cited by examiner

A)

B)

C)

D)

E)

F)

G)

H)

DEVICE AND METHOD FOR PRODUCING SPACERS

CROSS-REFERENCE TO RELATED APPLICATIONS

This application claims priority to European Patent Application No. 20191372.0, filed on Aug. 17, 2020, the entirety of which is incorporated herein by reference.

The invention relates to a device for producing a spacer by curing bone cement paste. The spacer is provided as a temporary placeholder in medical applications for temporarily replacing a joint or part of a joint comprising an articulating surface of a joint head. The spacer is preferably suitable and provided for temporarily replacing a hip joint or a shoulder joint and particularly preferably for temporarily replacing a hip joint. The device is accordingly preferably provided for producing a hip joint spacer or a shoulder joint spacer. The invention also relates to a set and to a method for producing such a spacer with such a device.

The present invention accordingly in particular provides a device in the form of a two-part casting mold for producing one-part hip and shoulder spacers, wherein the casting mold has a head mold and a stem mold and a metal core is used for constructing the spacer. Hip and shoulder spacers are intended as temporary placeholders (spacers) for the interim phase in the context of two-stage revisions of infected hip and shoulder total joint endoprostheses. The device is suitable for producing hip and shoulder spacers with low-viscosity and high-viscosity polymethyl methacrylate bone cement paste.

Joint endoprostheses, such as hip joint endoprostheses and shoulder joint endoprostheses, are widely implanted worldwide. Unfortunately, in a small percentage of cases, joint endoprostheses are colonized by microbial microorganisms, in particular Gram-positive bacteria as well as Gram-negative bacteria, and to a very small extent by yeasts and fungi. These microbial microorganisms, mainly typical skin microbes such as *Staphylococcus aureus* and *Staphylococcus epidermidis*, may enter a patient's body during a surgical operation (OP). It is also possible for microbial microorganisms to enter joint endoprostheses hematogenically. When joint endoprostheses are colonized by microbial microorganisms, the surrounding bone and soft tissue also become infected and damaged by the microbial microorganisms.

The prior art primarily encompasses two treatment methods for infected joint endoprostheses, one-stage septic revision and two-stage septic revision. In the case of one-stage revision, the infected joint endoprosthesis is removed first, next radical debridement is performed and then a revision joint endoprosthesis is implanted within one OP.

In two-stage septic revisions, in a first OP the infected joint endoprosthesis is initially removed, then debridement is performed and thereafter a spacer is implanted. A hip joint spacer consists of a stem, a collar, a neck and a ball head and replicates hip joint endoprostheses in shape and size. Similarly, a shoulder joint spacer replicates a shoulder joint endoprosthesis in shape and size. The spacer is anchored with bone cement to the respective bone, i.e. for example in the case of hip joint spacers to the proximal femur or in the femoral canal. The spacer remains for up to several weeks in the patient until the inflammation has subsided and clinical inflammation markers have receded. The spacer is then removed in a second OP and a revision joint endoprosthesis implanted after fresh debridement.

Spacers are of major significance as temporary placeholders in the interim phase in the context of two-stage septic replacement operations for hip and shoulder total joint endoprostheses. During intraoperative production of these spacers, medical personnel, depending on the available antibiogram of the microbial microorganisms responsible for the infection, add to the polymethyl methacrylate bone cement one or more antibiotic(s) specifically tailored to the microorganisms.

In the case of spacers, antibiotics are added to the cement powder before actual spacer production. Using this antibiotically modified bone cement powder, a bone cement paste is then produced by admixing monomer liquid and spacers are cast from this bone cement paste which then cure by polymerization with the assistance of the monomer liquid added to the cement powder. The bone cement paste thus substantially incorporates the antibiotics. The antibiotic particles situated in areas close to the surface are released under the action of bodily fluids, such as wound secretions. Active ingredient release is greatest at the start and then diminishes over the course of several days.

US 2010/0042213 A1 discloses a hip joint prosthesis with a reservoir for liquid inside the implant. A hip spacer is known from WO 2017/178951 A1 which has indentations, wherein a substance for treating the bone may be introduced into the indentations. U.S. Pat. No. 6,245,111 B1 proposes a hip joint prosthesis, the surfaces of which are coated with an antibiotic. U.S. Pat. No. 5,681,289 discloses a device for distributing a liquid active ingredient with the assistance of a bladder inside the device. None of the stated prostheses is suitable for producing an irrigation circuit. EP 1 991 170 B1 and US 2011/0015754 A1 describe a hip joint spacer containing active ingredients. US 2019/0290833 A1 discloses an irrigatable hip joint spacer, with which a liquid circuit is producible. WO 2016/205077 A1 and U.S. Pat. No. 8,900,322 B2 describe further spacers with an irrigation function.

It is known to use spacers provided with antibiotics. Spacers may on the one hand be produced by the OP personnel during the OP itself from PMMA bone cement powder, antibiotics and monomer liquid, for example with a spacer mold, as described for example in patents DE 10 2015 104 704 B4 or EP 2 617 393 B1; on the other hand it is also conventional to use hip joint spacers prefabricated industrially from bone cement.

Plastics casting molds are conventional for the intraoperative production of spacers with polymethyl methacrylate bone cement. Plastics casting molds for intraoperative production of one-part hip spacers are described in U.S. Pat. No. 6,361,731 B1. These casting molds are transparent and have two separate filling openings. As a result, even high-viscosity bone cement paste can be introduced into the casting mold with little pressure, because the flow paths for the bone cement paste are relatively short. When using non-high-viscosity bone cement paste, the risk arises, once filling of the casting mold is complete, of bone cement paste flowing back out of the filling openings before curing begins. These casting molds are offered for sale with different spacer head diameters. The diameter of the spacer head is not variably adjustable. The medical user can only select between predetermined spacer head sizes. It would be desirable for the medical user as far as possible with one casting mold for the stem to be able to choose between different spacer head sizes.

In a further development, patent specifications U.S. Pat. No. 7,789,646 B2, U.S. Pat. No. 8,480,389 B2 and U.S. Pat. No. 8,801,983 B2 propose multipart casting molds for the production of modular hip spacers. These modular hip spacers consist of a spacer head and a separate stem. Casting molds for the spacer head with different spacer head diameters are available for this purpose. This means that the casting mold for the stem is connected to the casting mold for the spacer head which has the selected diameter. The casting mold assembled in this manner is then one-part and has a thread at the filling opening for connecting the casting mold to a cement cartridge. Another variant according to U.S. Pat. No. 7,637,729 B2 uses a casting mold for producing the stem and a separate casting mold for the spacer head. After completion of curing and demolding, the two spacer components are assembled. U.S. Pat. No. 7,789,646 B2 describes a modular casting mold in which the filling opening of the casting mold can be closed using a plug once the cement paste has been introduced into the casting mold. Before that, however, the casting mold has to be unscrewed from the cement cartridge. When using low-viscosity cement paste, it is therefore possible, if the casting mold is held in an unfavorable way, for cement paste to run out during separation of the casting mold from the cement cartridge before the plug has been screwed in. When using non-high-viscosity bone cement paste, it is therefore possible, if the casting mold is held in an unfavorable way, for bone cement paste to run out during separation of the casting mold from the bone cement cartridge before the plug has been screwed in or inserted. In either case, unwanted entrapped air may occur in the spacer mold due to the bone cement paste coming away from the inner wall of the casting mold.

One problem associated with the listed devices is that the bone cement paste must have a relatively low viscosity so that the bone cement paste can flow around the metal core and the casting mold can be completely filled with the cement paste.

US 2007/0222114 A1 describes a hip spacer mold. This spacer mold consists of a plurality of mold segments which are connected together. Thanks to the plurality of segments, the spacer mold may be adapted very precisely to the patient's anatomical circumstances. The spacer mold segments are joined together by means of worm drive hose clips. A PMMA bone cement paste (polymethyl methacrylate bone cement paste) is introduced through channels in the spacer mold. The complex structure of the casting mold makes it very complicated to join the spacer mold segments together and to remove the hip spacer once curing of the PMMA bone cement paste is complete.

WO 2009/073 781 A2 proposes a spacer mold for a hip spacer consisting of two parts which may be displaced relative to one another in order to enable adaptation of the length of the stem. A further casting mold is disclosed in EP 2 522 310 A1. This device consists of at least two parts, wherein an insertion portion is arranged in a first part and an insertion receptacle is arranged in the second part. The two parts are insertable into one another and form a casting mold for producing the stem of the hip spacer. EP 2 787 928 A1 describes a complex casting mold. This enables the production of hip spacers with different ball heads. The elements of the casting mold are fixed in place using connecting elements.

The object of the present invention thus consists in overcoming the disadvantages of the prior art. In particular, the object of the invention consists in the development of a simple and inexpensive device and a set for producing a one-part spacer by curing bone cement paste and in the development of a method which can be carried out simply and inexpensively for producing a one-part spacer by curing bone cement paste, with which one-part spacers, in particular hip and shoulder spacers, can be produced by medical personnel during the OP using bone cement paste, in particular polymethyl methacrylate bone cement paste. Hip and shoulder spacers are of similar construction. They consist of a stem and a spacer head as well as a neck which connects the stem and the spacer head. In particular, it is intended to be possible to produce spacers with different, predetermined head diameters and different neck lengths, wherein it is intended to be possible for the offset (neck length), i.e. the distance of the spacer head from the stem, of the spacer to be produced to be individually adjustable on the casting mold by medical personnel.

It is intended to be possible to produce spacers, in particular hip spacers, using not only low-viscosity but also high-viscosity (polymethyl methacrylate) bone cement paste. In particular, it is intended to be possible to produce spacers with high-viscosity cement paste without the use of particular manual force. The casting mold is intended to be made up of a maximum of two hollow plastics parts which can straightforwardly be produced as inexpensively as possible, for example by plastics injection molding or by thermoforming plastics films. The casting mold is intended to contain a metal core of a biocompatible metal for mechanically reinforcing the hip spacer. The casting mold to be developed is intended to have neither one nor a plurality of sprues. The spacers to be produced should therefore be such that they have no sprue. The intention is as a consequence to avoid costly mechanical post-processing of the produced spacers. The intention is furthermore to develop a set or kit with which it is possible to produce spacers, in particular hip spacers, with different head sizes and offsets corresponding to the patient's particular individual anatomical conditions. The intention is moreover to describe a maximally simple method for producing hip spacers.

The intention is therefore to develop a device, in particular with a casting mold and a metal core, which is in principle suitable for the production of hip and shoulder spacers while ensuring the simplest and most inexpensive structure possible. The intention is for a metal core to be or have been arranged inside the hip and shoulder spacer for the purpose of mechanical stabilization. The intention is for it to be possible to produce spacers using not only low or non-high-viscosity but also high-viscosity (polymethyl methacrylate) bone cement paste. A high injection pressure is conventionally needed for completely filling a casting mold with a high-viscosity bone cement paste. It would be helpful if this could be avoided.

The objects of the invention are achieved by a device for producing a spacer by curing bone cement paste, wherein the spacer is provided in the medical field for temporarily replacing a joint or part of a joint comprising an articulating surface of a head of the joint, in particular for temporarily replacing a hip joint or a shoulder joint, the device having a stem mold for shaping a stem of the spacer from bone cement paste, wherein the stem mold has in the interior thereof an inner space, wherein the inner space is accessible via a proximal opening on a proximal side of the stem mold and wherein the stem mold has a proximal wall which peripherally delimits the proximal opening of the stem mold, a head mold for shaping a head and a neck of the spacer from bone cement paste, wherein the head mold has in the interior thereof a hollow space, wherein the hollow space has a spherical surface-shaped inner surface for shaping a sliding surface of the head of the spacer and the hollow space is accessible via a distal opening on a distal side of the head mold, wherein the head mold has a distal wall which peripherally delimits the distal opening of the head mold, and having a metal core, wherein the metal core has a stem part, a head part and a flange, wherein the flange projects out from the metal core, wherein the flange is arranged between the stem part and the head part and wherein the flange has a proximal surface and a distal surface, wherein the stem mold and the stem part of the metal core are shaped such that the stem part is arranged in the inner space of the stem mold, when the proximal wall of the stem mold is resting against the distal surface of the flange, and wherein the head mold and the head part of the metal core are shaped such that the head part is arranged in the hollow space of the head mold when the distal wall of the head mold is resting against the proximal surface of the flange.

Provision may preferably be made according to the invention for the proximal wall of the stem mold to be placeable flush against the distal surface of the flange and/or the distal wall of the head mold to be placeable flush against the proximal surface of the flange.

The stem mold and the stem part of the metal core are preferably shaped such that the stem part is completely arranged in the inner space of the stem mold, when the proximal wall of the stem mold is resting against the distal surface of the flange, in particular is resting flush against the distal surface of the flange.

The head mold and the head part of the metal core are likewise preferably shaped such that the head part is completely arranged in the hollow space of the head mold, when the distal wall of the head mold is resting against the proximal surface of the flange, in particular is resting flush against the proximal surface of the flange.

The metal core preferably consists of a biocompatible metal.

The flange may be continuously peripherally shaped or also have one or more interruptions.

The device is particularly preferably a device for producing a hip spacer.

Provision may be made for the metal core to be arranged in its entirety or apart from the flange within the stem mold and the head mold.

The flange preferably projects out transversely or radially from the metal core.

The proximal surface of the flange limits possible displacement of the head mold in the distal direction of the metal core and the distal surface of the flange limits possible displacement of the stem mold in the proximal direction of the metal core.

In a preferred development, the flange takes the form of circumferential collar around the metal core, wherein the collar annularly surrounds the metal core or is arranged as an elliptical collar inclined relative to a stem of the metal core. A circumferential collar has the advantage that a secure limit stop of the head mold and of the stem mold is provided.

The statements of direction proximal and distal and transverse are understood to correspond to anatomical directional designations. Distal here means away from the center of the body and proximal means towards the center of the body. With regard to the spacer and the device for producing the spacer, the directional designations are used as would be correct for the spacer or the spacer produced therewith in the state in place in the patient.

A cylinder and cylindrical geometry is here taken to mean a general cylinder. A general cylinder is obtained by linear displacement of a base area, in this case the base area which is delimited by the peripheral edge of the cavity. In a right cylinder, displacement proceeds perpendicularly to this base area while in a skewed cylinder it proceeds at an angle other than 90°.

Provision may be made according to the invention for the metal core to consist of the stem part, the head part and the flange and/or for the metal core to be one-part.

In this way, the metal core in the interior of the spacer can better absorb the forces which arise and the device is simple to construct and use.

Provision may also be made for the stem mold and/or the head mold to consist of a plastics material and preferably of at least one plastics film or of an injection-molded plastics material.

In this way, the device is inexpensive to construct and easily usable. In addition, once used, the stem mold and the head mold may accordingly be disposed of easily, inexpensively and above all hygienically by incineration.

Provision may further be made for the stem part to be spaced in the inner space of the stem mold from inner walls of the stem mold which delimit the inner space, when the proximal wall of the stem mold is resting against the distal surface of the flange, in particular is resting flush against the distal surface of the flange, and/or for the head part to be spaced in the hollow space of the head mold from inner walls of the head mold which delimit the hollow space, when the distal wall of the head mold is resting against the proximal surface of the flange, in particular is resting flush against the proximal surface of the flange.

In this way, the metal core can be successfully arranged centered in the head mold or in the stem mold, such that said core is surrounded by a uniformly thick layer of the bone cement paste.

Provision may moreover be made for the head mold to have a neck mold for shaping a neck of the spacer, which neck connects the head and the stem, from bone cement paste, wherein the neck mold is tubular or hollow-cylindrical, wherein the distal opening and the distal wall of the head mold are both parts of the neck mold and the spherical surface-shaped inner surface of the hollow space is not part of the neck mold, wherein the head mold and the head part of the metal core are preferably shaped such that the head part protrudes beyond the neck mold into the hollow space of the head mold, when the distal wall is resting against the proximal surface of the flange.

Thanks to the neck mold, it is possible to put the head mold and thus the device to variable use for producing differently shaped spacers with different neck lengths. The neck mold of the head mold can be straightforwardly shortened with scissors, a knife, a scalpel or a saw.

Provision may here be for the length of the neck mold to be adjustable by shortening the neck mold, wherein, preferably, predetermined cutting or tearing points are arranged on the neck mold and/or a scale is arranged externally on the neck mold.

In this way, the device can be used particularly quickly and uncomplicatedly.

Provision may further be made for the proximal surface of the flange to limit displacement of the metal core in the head mold, in particular in the neck mold, and/or for the distal surface of the flange to limit displacement of the metal core in the stem mold.

In this manner, the flange creates a limit stop for the head mold and/or the stem mold, such that the device is simply usable and assemblable.

According to a preferred embodiment, provision may be made for centering means to be arranged on the head part of the metal core, wherein the centering means project out from the surface of the head part, wherein the centering means space inner walls of the head mold from the head part, when the stem part of the metal core is pushed into the hollow space of the head mold, in particular space the neck mold walls of the head mold from the head part, when the stem part of the metal core is pushed into the hollow space of the head mold, wherein the centering means are preferably centering fins and the head part of the metal core is axially displaceable along the centering fins in the head mold, in particular is displaceable in the neck mold, and/or spacing pieces are arranged on the stem part of the metal core, wherein the spacing pieces project out from the surface of the stem part, wherein the spacing pieces space inner walls of the stem mold from the stem part of the metal core, when the stem part of the metal core is pushed into the inner space of the stem mold.

This ensures that the head part of the metal core is centered in the head mold and/or the stem part of the metal core is centered in the stem mold and bone cement paste can surround or flow around said parts on all sides. This additionally simplifies assembly of the parts of the device during production of the spacers. The spacing pieces ensure that the metal core is spaced from the outside of the stem to be cast.

The proximal surface of the flange limits axial displacement of the head mold parallel to the centering means or to the centering fins in the distal direction of the metal core and the distal surface of the flange limits displacement of the stem mold in the proximal direction of the metal core.

The centering means or centering fins in particular rest against the inner interior edge of the hollow-cylindrical neck mold of the head mold and center the head mold such that the axis of the head mold lies on the axis of the proximal metal core. The hollow-cylindrical neck mold of the head mold can be manually shortened in line with the patient's anatomical requirements, such that the offset can be individually adjusted. The advantage here is that as a result the spacer neck and spacer head are in one piece and the two parts of the hip spacer are consequently securely interconnected. There is no need for assembly steps for fastening the spacer head to the neck or to the stem of the hip spacer as set out in patent specifications U.S. Pat. No. 7,789,646 B2, U.S. Pat. No. 8,480,389 B2 and U.S. Pat. No. 8,801,983 B2.

The centering means and/or the spacing pieces are preferably embodied in one part with the metal core. This further simplifies the device.

Provision may moreover be made for the outer circumference of the flange to be larger than the proximal opening of the stem mold and/or than the distal opening of the head mold.

In this way, it is possible to prevent the flange being inadvertently and excessively deeply pushed through the distal opening of the head mold into the hollow space of the head mold or through the proximal opening of the stem mold into the inner space of the stem mold. It is additionally ensured that the distal edge (the distal wall) of the head mold is reliably limited in the axial movement thereof relative to the metal core.

Provision may also be made for the at least one vent opening to be arranged in the stem mold and/or head mold, wherein the at least one vent opening gas-permeably connects the inner space of the stem mold and/or the hollow space of the head mold with the surroundings of the device, wherein the at least one vent opening is preferably permeable to gases and impermeable to bone cement paste, in particular is impermeable to polymethyl methacrylate bone cement paste.

In this way, it is possible to ensure that entrapped air can more readily escape from the inner space of the stem mold or from the hollow space of the head mold. This prevents unwanted defects on the surface of the spacer.

Provision may further be made for the device to have a cement powder packaged in at least one microbe-proof cement container and a monomer liquid packaged in at least one microbe-proof and liquid-tight monomer liquid container.

This further completes the device. The device is then immediately ready to produce a spacer.

Provision may here be made for the device to have at least one bone cement cartridge for mixing the cement powder with the monomer liquid and for delivering mixed bone cement paste from the bone cement cartridge and preferably to have a bone cement cartridge for mixing polymethyl methacrylate bone cement starting components and for delivering mixed polymethyl methacrylate bone cement paste from the bone cement cartridge, wherein particularly preferably the at least one bone cement cartridge has the at least one cement container and contains the at least one monomer liquid container, wherein the at least one cement container and the at least one monomer liquid container are arranged in mutually separate regions.

In this way, the bone cement paste produced with the bone cement cartridge can be conveniently introduced into the stem mold and the head mold.

The objects underlying the invention problem are also achieved by a set for producing different spacers by curing bone cement paste, wherein the spacers are provided in the medical field for temporarily replacing a joint or part of a joint comprising an articulating surface of a head of the joint, in particular for temporarily replacing a hip joint or a shoulder joint, the set having at least one device according to the invention as described above, wherein the set has at least two head molds with different diameters of the spherical surface-shaped inner surfaces and/or at least two stem molds with hollow spaces of different lengths in the distal direction or different internal diameters of the hollow spaces.

In this way, a variable set is provided with which it is possible to produce differently shaped spacers which are suited to a plurality of different treatment situations.

The set is particularly preferably a set for producing a hip spacer.

Provision may be made for the set to have at least two metal cores with a different length of the head part and/or of the stem part.

The set is still more variable as a result.

The objects underlying the present invention are also achieved by a method for producing a spacer for temporarily replacing a joint or part of a joint, in particular a hip joint or a shoulder joint, comprising an articulating surface of the joint, wherein the method is carried out with a device according to the invention or with a set according to the invention, the method having the following steps:

A) introducing a bone cement paste into the inner space of the stem mold and introducing a bone cement paste into the hollow space of the head mold;

B) pushing the head part of the metal core into the hollow space, filled with bone cement paste, of the head mold, so displacing the bone cement paste contained therein, until the distal wall of the head mold is resting against the proximal surface of the flange of the metal core, and pushing the stem part of the metal core into the inner space, filled with bone cement paste, of the stem mold, so displacing the bone cement paste contained therein, until the proximal wall of the stem mold is resting against the distal surface of the flange of the metal core;

C) curing the bone cement paste in the head mold and the stem mold; and

D) removing the resultant shaped and cured spacer from the head mold and the stem mold.

The method is particularly preferably a method for producing a hip spacer.

The method preferably does not comprise a step for therapeutic or medical treatment of a human or animal body. The method merely relates to the production of a spacer which can then be put to medical use. The latter does not, however, proceed in the course of the method according to the invention.

Step C) proceeds after steps A) and B) and step D) proceeds after step C). Steps A) and B) may proceed not only in succession but also in parallel.

Provision may be made before step A) for a neck mold of the head mold to be shortened in accordance with a desired length of the neck of the spacer to be produced, a head mold with a matching internal diameter of the spherical surface-shaped inner surface is selected to match the desired shape of the head of the spacer to be produced, a stem mold with an inner space matching the desired shape of stem of the spacer to be produced is selected and/or a metal core with dimensions matching the desired shape of the stem of the spacer to be produced is selected.

In this way, a variable method is provided with which it is possible to produce differently shaped spacers which are suited to a plurality of different treatment situations.

Provision may moreover be made before step A) for the homogeneous bone cement paste to be produced by mixing a monomer liquid and a cement powder, wherein preferably in step A) the mixed bone cement paste is pressed with a bone cement cartridge into the inner space of the stem mold and into the hollow space of the head mold, wherein particularly preferably in so doing the air is expelled from the inner space of the stem mold and from the hollow space of the head mold.

This further perfects the method.

Provision may also be made in step B) for the head part of the metal core to be centered in the head mold with the assistance of centering means, in particular with the assistance of centering fins, which project out from the surface of the head part and which, when the head part is pushed into the hollow space of the head mold, rest against inner walls of the hollow space of the head mold, and/or in step B) for the stem part of the metal core to be centered in the stem mold with the assistance of spacing pieces, which project out from the surface of the stem part and which, when the stem part is pushed into the inner space of the stem mold, rest against inner walls of the inner space of the stem mold.

This ensures that the head part of the metal core is centered in the head mold and/or the stem part of the metal core is centered in the stem mold and bone cement paste can surround or flow around said parts on all sides. This additionally simplifies assembly of the parts of the device during production of the spacers.

The invention is based on the surprising recognition that a head mold and a stem mold can be filled to excess with a bone cement paste and they can be pushed onto a metal core with a suitable flange as limit stop, such that the excess bone cement paste is pressed out of the assembled casting mold and the metal core is enclosed in places in the bone cement paste in the assembled casting mold. In this way, it is possible according to the invention to avoid having to press in the bone cement paste through the interspaces between the metal core and the inner walls of the head mold and the stem mold, something which, in particular with a high-viscosity bone cement paste, requires considerable pressure and application of force. As a result, the head mold and the stem mold can in turn be inexpensively fabricated from simple plastics and can therefore be simply produced, for example by plastics injection molding or by thermoforming plastics films. The excess bone cement paste which has emerged from the head mold and the stem mold can be removed and discarded before or after the bone cement paste cures in the casting mold.

According to the invention, the stem mold and the head mold can be inexpensively produced from plastics material by injection molding or can even also be produced from a thermoformed plastics film since, even during introduction of a high-viscosity bone cement paste, they do not have to withstand any very large forces. This is possible because according to the invention the bone cement paste is introduced into the two parts of the casting mold without the metal core already being arranged therein and consequently having to be flowed around. Arranging the metal core in the stem mold and in the head mold subsequent to the introduction of the bone cement paste is possible because the stem mold and the head mold are placed against the flange of the metal core and are accordingly arranged and oriented to fit with the metal core and with one another. As a result, there is no need for the stem mold and the head mold to be screwed or fastened together in a costly, pressure-resistant manner.

A further particular advantage of the present invention is that, using the head mold, it is possible to produce a variable cylindrical region, which may be denoted neck mold and which, for forming a neck of the spacer, connects the head of the spacer to the stem of the spacer, by the cylindrical region having to be manually shortened depending on the particular patient's anatomical requirements. Differently shaped head molds can be used and selected for producing spacers with different head diameters. The other dimensions can also be adapted with a set according to the invention by differently shaped stem molds and differently shaped metal cores.

The device according to the invention is used in such a manner that bone cement paste is firstly retrogradely introduced into the head mold. A mixing system or cartridge system as bone cement applicator with a cartridge and a manually operable expulsion device may be used for this purpose. The proximal head part of the metal core is then pressed into the head mold filled with bone cement paste. The proximal head part of the metal core penetrates into the bone cement paste until the distal wall as the edge of the head mold or the edge of the hollow-cylindrical neck part of the head mold comes into contact with the proximal surface of the flange. The flange limits axial movement of the head mold. The stem mold is then retrogradely filled with bone cement paste. Thereafter, the stem part of the metal core is pressed into the stem mold filled with bone cement paste until the proximal wall as the edge of the stem mold comes to a stop on the distal surface of the flange. The excess expelled bone cement paste emerges from the opening of the stem mold and is manually removed. The bone cement paste is then left to cure. Thereafter, the head mold is removed by being cut open and the stem mold is pulled off the cured stem of the spacer which has been formed. The spacer can also be fabricated with the device according to the invention such that firstly the stem mold and thereafter the head mold are filled with bone cement paste. In this case too, the metal core is pressed into the molds filled with bone cement.

The device according to the invention is based on the surprising finding that a metal core can be pressed with less force into a casting mold filled with bone cement paste than bone cement paste can be pressed around a metal core arranged in the casting mold by pressure force generated by manually actuatable expulsion devices as is necessary in known casting devices according to patent specifications U.S. Pat. No. 7,789,646 B2, U.S. Pat. No. 8,480,389 B2 and U.S. Pat. No. 8,801,983 B2.

As a result, it is possible to produce spacers within a few minutes even from a high-viscosity bone cement paste without using a high pressure force. Pressure-resistant casting molds are not necessary. The casting mold according to the invention is filled virtually without pressure and can therefore be fabricated from thin plastics films or injection-molded plastics articles.

An exemplary device according to the invention may be composed of
- a) a metal core which consists of a head part and a stem part, wherein the head part is separated from the stem part by one or more flanges which are arranged on the surface of the metal core, wherein the at least one flange has a proximal side (surface) and a distal side (surface),
- b) a hollow spacer head mold or head mold fabricated from a plastics material with a hollow-cylindrical neck mold,
- c) a hollow stem mold fabricated from a plastics material, wherein
- d) the head part of the metal core protrudes into an inner space of the head mold, when the hollow-cylindrical neck mold is resting against the proximal side of the at least one connecting piece and the stem part of the metal core is completely surrounded by the stem mold, when the stem part is resting with the opening thereof against the distal face of the at least one flange.

An exemplary set according to the invention for producing spacers may be composed of
- a) a metal core which consists of a head part, a flange and a stem part,
- b) at least one stem mold, and
- c) at least two head molds with different head diameters which are arranged in a sterilizable microbe-proof packaging container.

The set according to the invention offers the advantage that spacers having different head sizes can be produced by the medical user with one packaging unit of the set. As a result, there is no need to provide separate packaging units for each spacer head size.

A further exemplary set according to the invention for producing spacers may be composed of
- a) a cement powder packaged in a microbe-proof container,
- b) a monomer liquid packaged in a microbe-proof, liquid-impermeable container,
- c) a metal core which consists of a head part, at least one flange and a stem part,
- d) at least one stem mold, and
- e) at least two head molds with different head diameters which are arranged in a sterilizable microbe-proof packaging container.

Such sets can be supplied to the medical user as "procedure packs". The set contains all the components necessary for the production of hip spacers.

An exemplary method according to the invention for producing spacers with the device according to the invention may comprise the following successive steps:

- a) mixing a cement powder with a monomer liquid until a homogeneous bone cement paste is obtained,
- b) introducing the bone cement paste into the head mold,
- c) introducing the bone cement paste into the stem mold,
- d) pushing the head part of the metal core into the head mold filled with bone cement paste, so displacing the bone cement paste, until the edge of the hollow-cylindrical neck mold of the head mold is resting against the proximal surface of the flange,
- e) pushing the stem part of the metal core into the stem mold filled with bone cement paste, so displacing the bone cement paste, until the proximal opening of the stem mold is resting against the distal surface of the flange,
- f) curing the bone cement paste, and
- g) removing the head mold and the stem mold once the bone cement paste has completely cured.

According to the invention, provision may be made before step a) for the length of the hollow-cylindrical neck mold of the head mold to be shortened in order to adjust the offset, i.e. to adjust the distance between the head and the stem of the spacer. To this end, the medical user uses scissors or a saw to shorten the hollow-cylindrical neck mold on the head mold to until the desired offset, the distance from the center of the spherical mold to the longitudinal axis of the metal core, is obtained.

Further exemplary embodiments of the invention are explained below with reference to twenty five schematic figures but without thereby limiting the invention. In the figures.

FIG. 24A) to H) shows a schematic cross-sectional view through eight devices differing with regard to the head mold for producing a hip spacer which can be used as a set according to the invention; and FIG. 25A) to H) shows a schematic side view of spacers which were produced with the devices according to FIG. 24A) to H).

FIGS. 1 to 25 show devices, sets and the parts thereof and method sequences which are provided for producing hip spacers. A person skilled in the art is straightforwardly capable of transferring this teaching to devices, sets and the parts thereof and method sequences for producing shoulder spacers.

Figure 1:
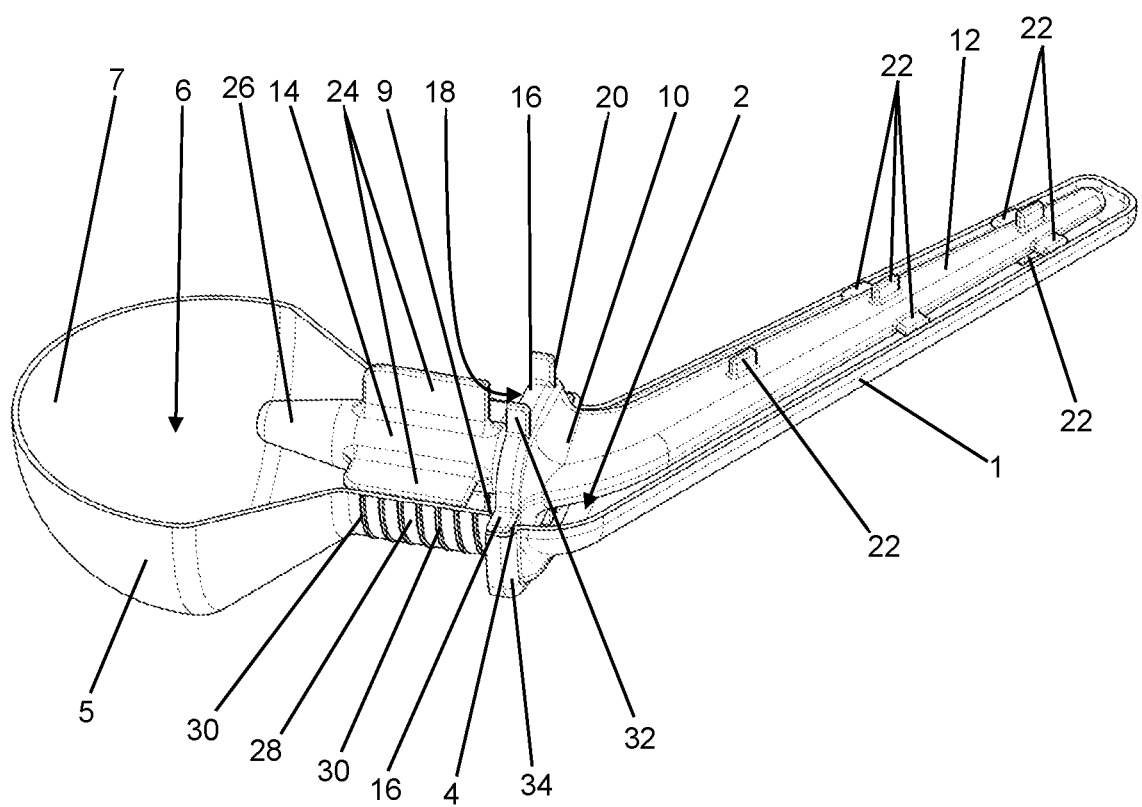
FIG. 1 shows a schematic perspective partial cross-sectional view of an assembled first exemplary device according to the invention for producing a hip joint spacer.
Figure 2:
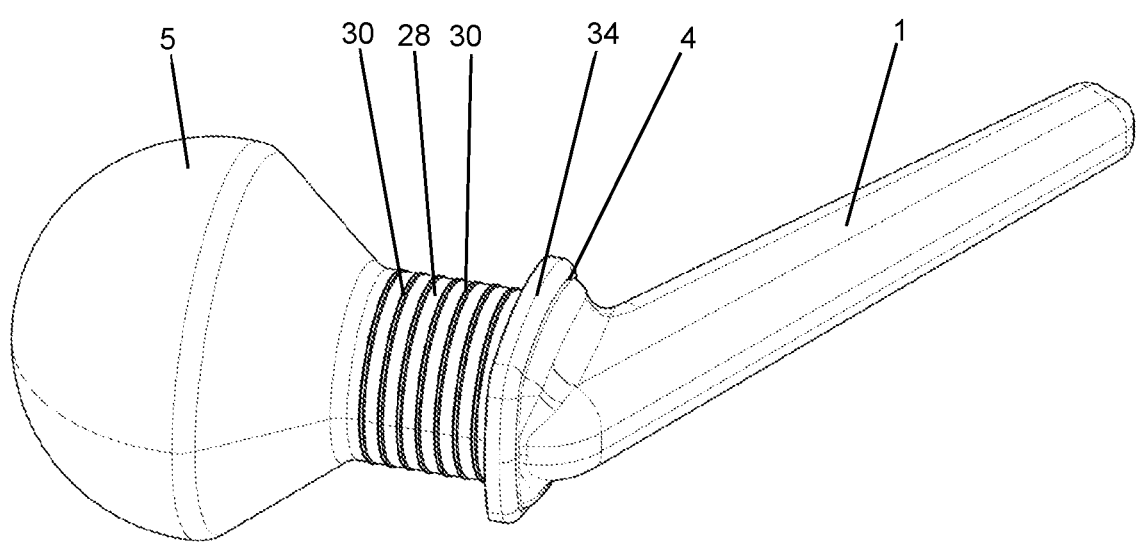
FIG. 2 shows a schematic perspective external view of the assembled first device according to the invention according to FIG. 1.
Figure 3:
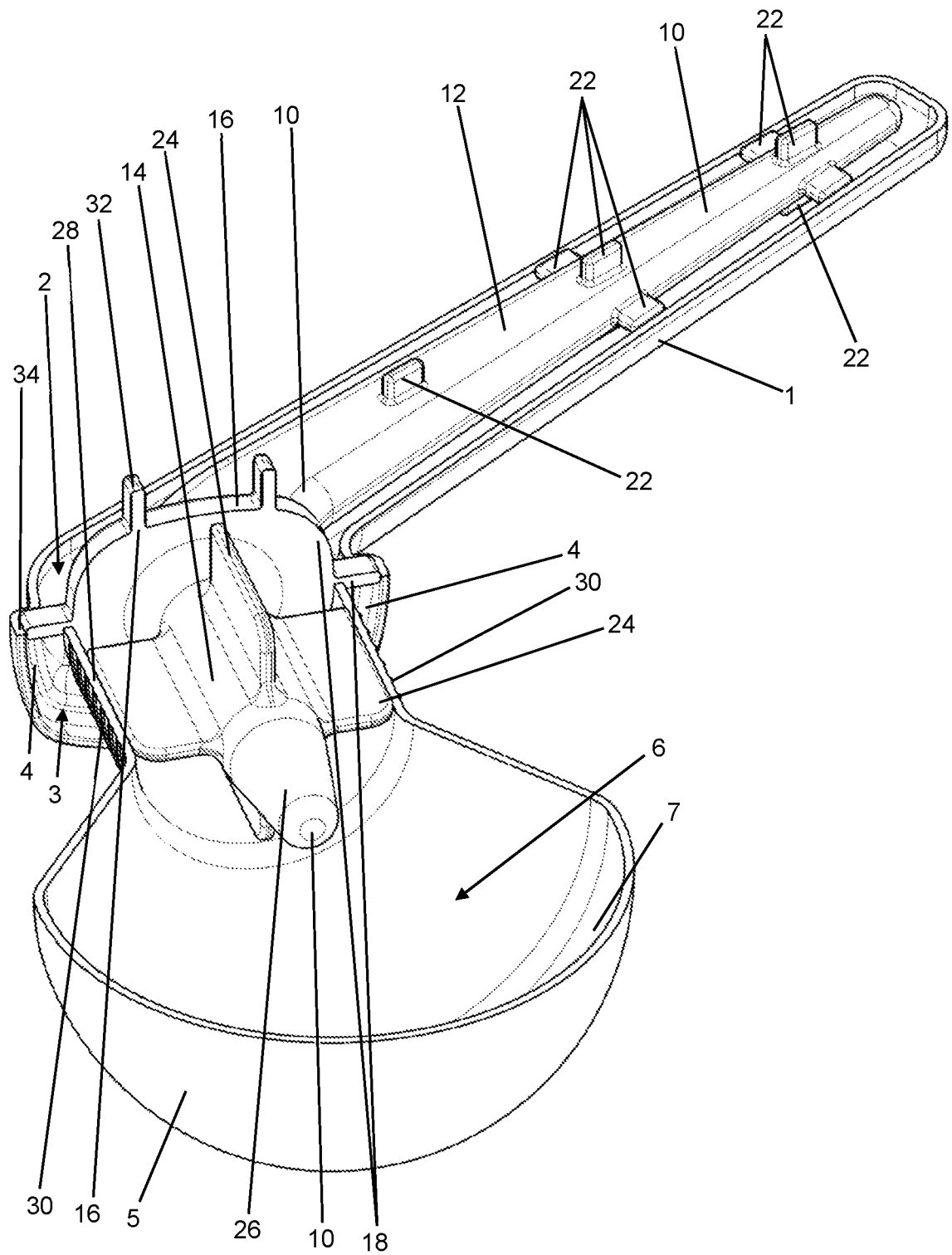
FIG. 3 shows a schematic perspective partial cross-sectional view of the assembled first device according to the invention according to FIGS. 1 and 2.
Figure 4:
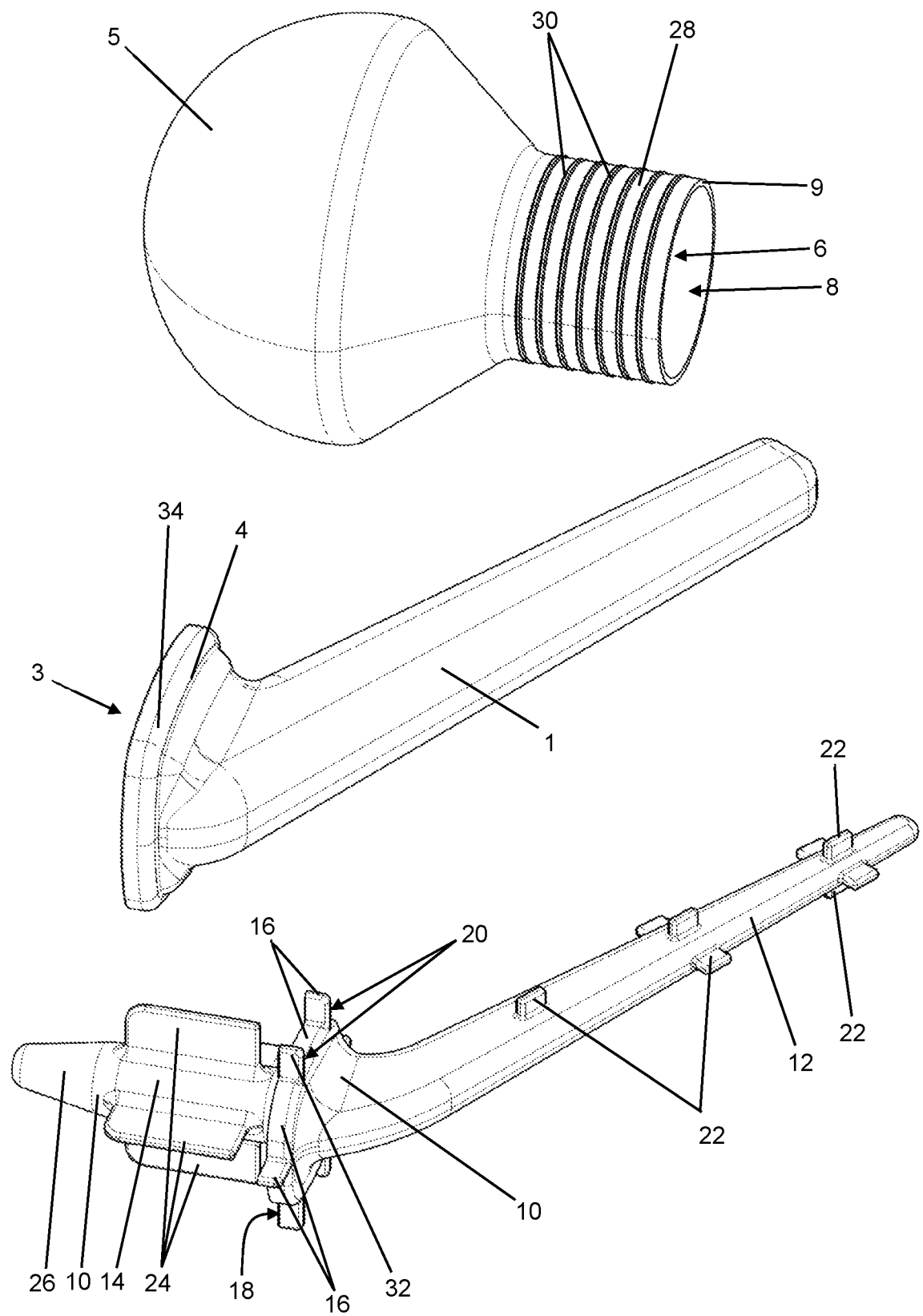
FIG. 4 shows a schematic perspective external view of the parts of the first device according to the invention according to FIGS. 1 to 3.
Figure 5:
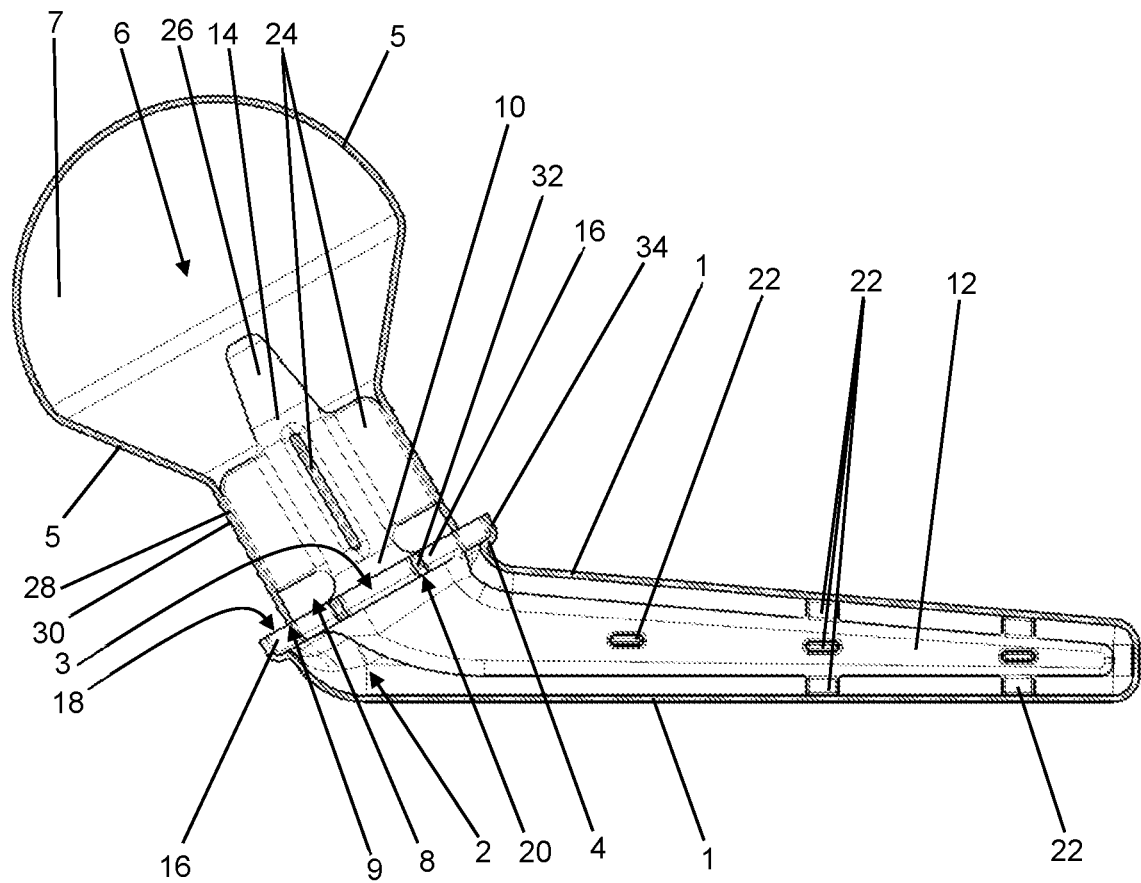
FIG. 5 shows a schematic partial cross-sectional view of the assembled first device according to the invention.
Figure 6:
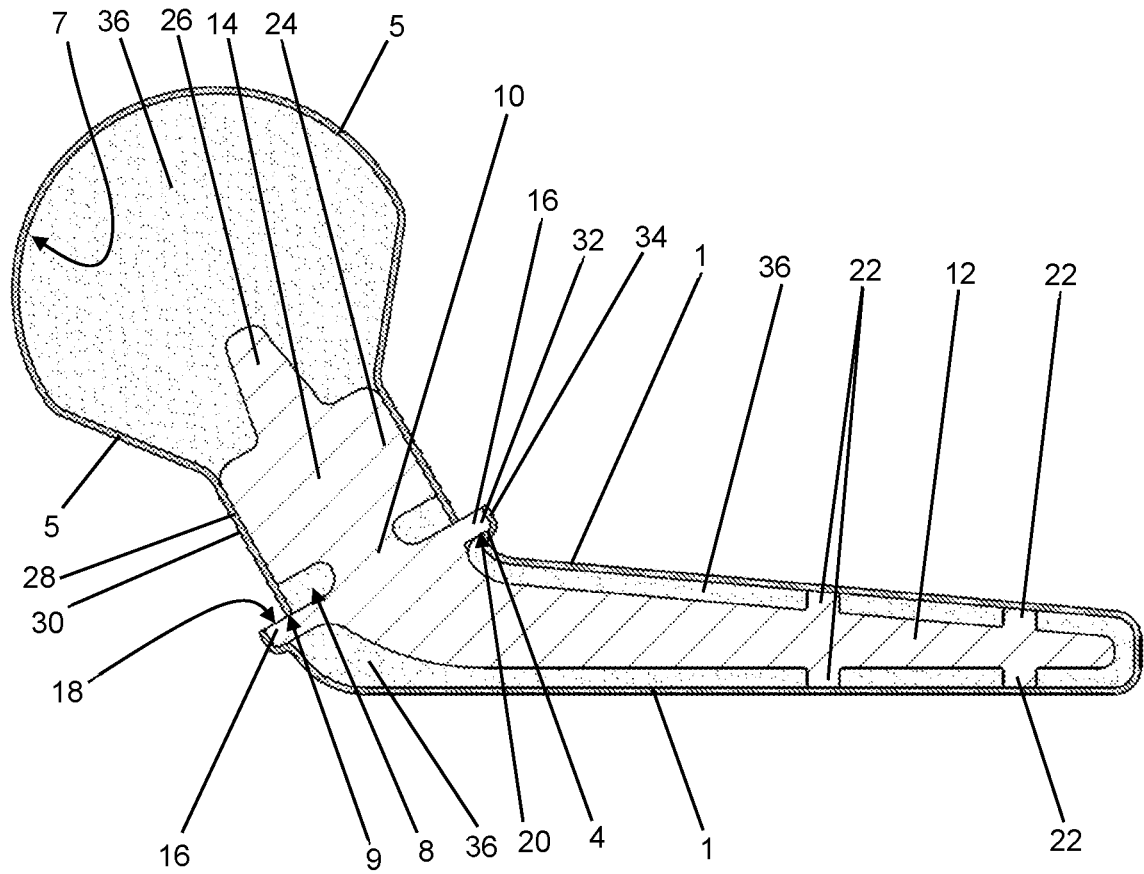
FIG. 6 shows a schematic cross-sectional view of the first device according to the invention with introduced bone cement paste.
Figure 7:
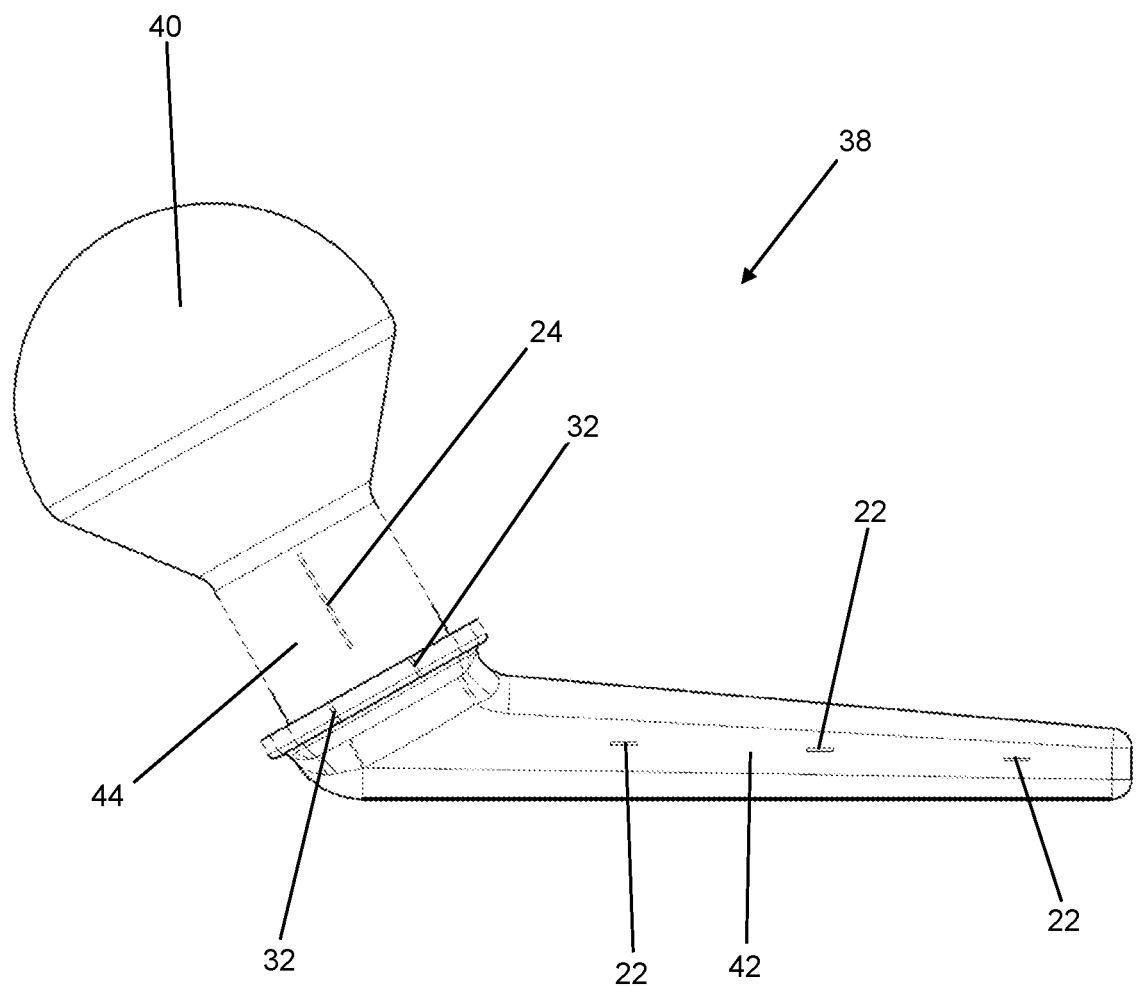
FIG. 7 shows a schematic side view of a hip spacer produced with the first device according to the invention.
Figure 8:
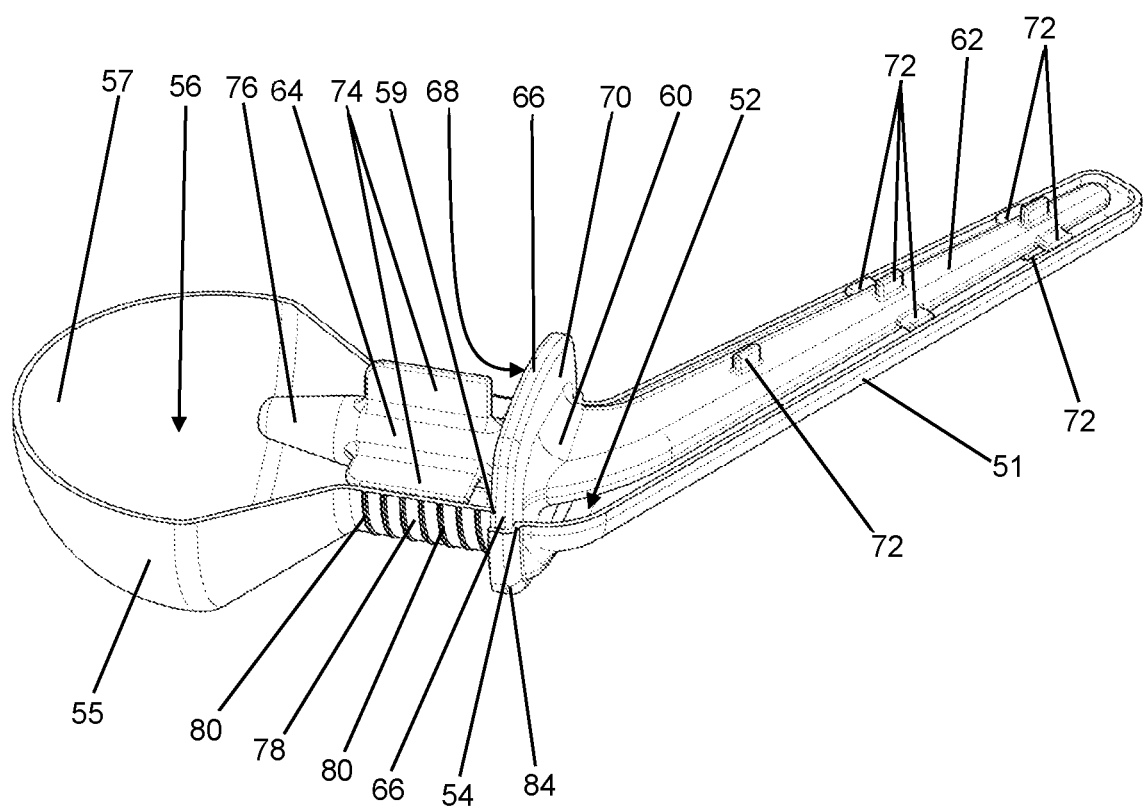
FIG. 8 shows a perspective partial cross-sectional view of an assembled second exemplary device according to the invention for producing a hip joint spacer.
Figure 9:
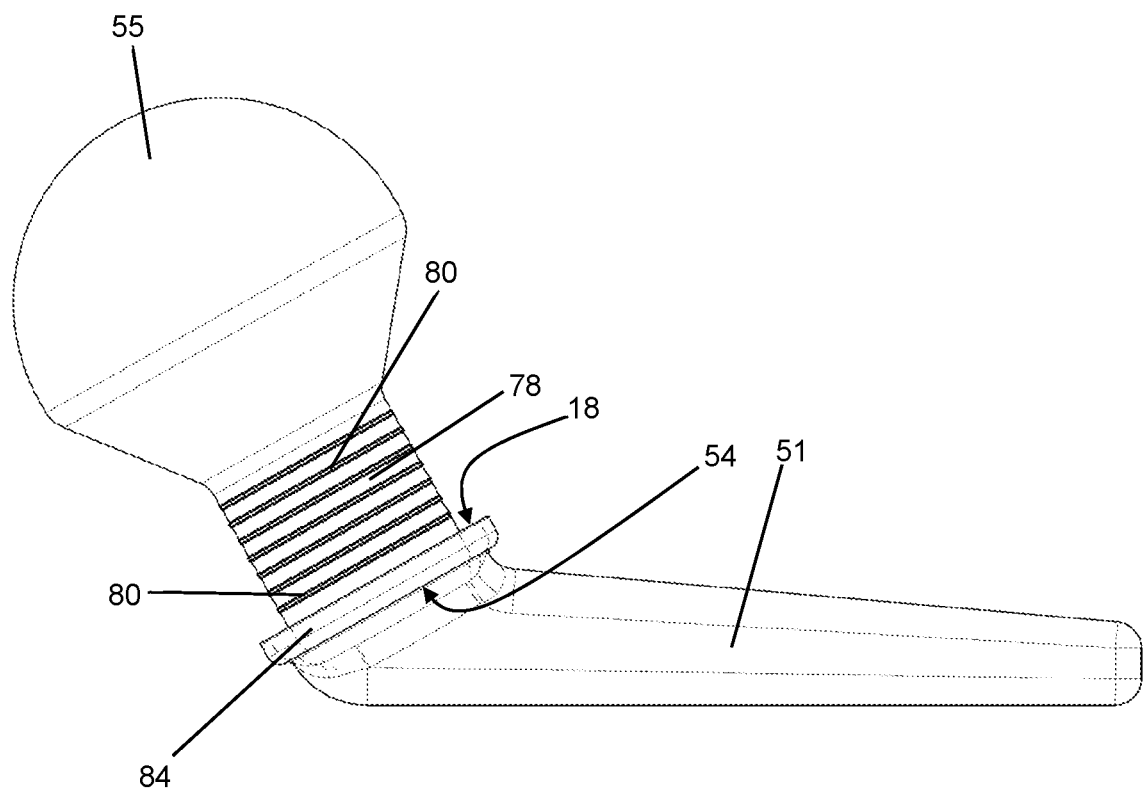
FIG. 9 shows a side view of the assembled second device according to the invention.
Figure 10:
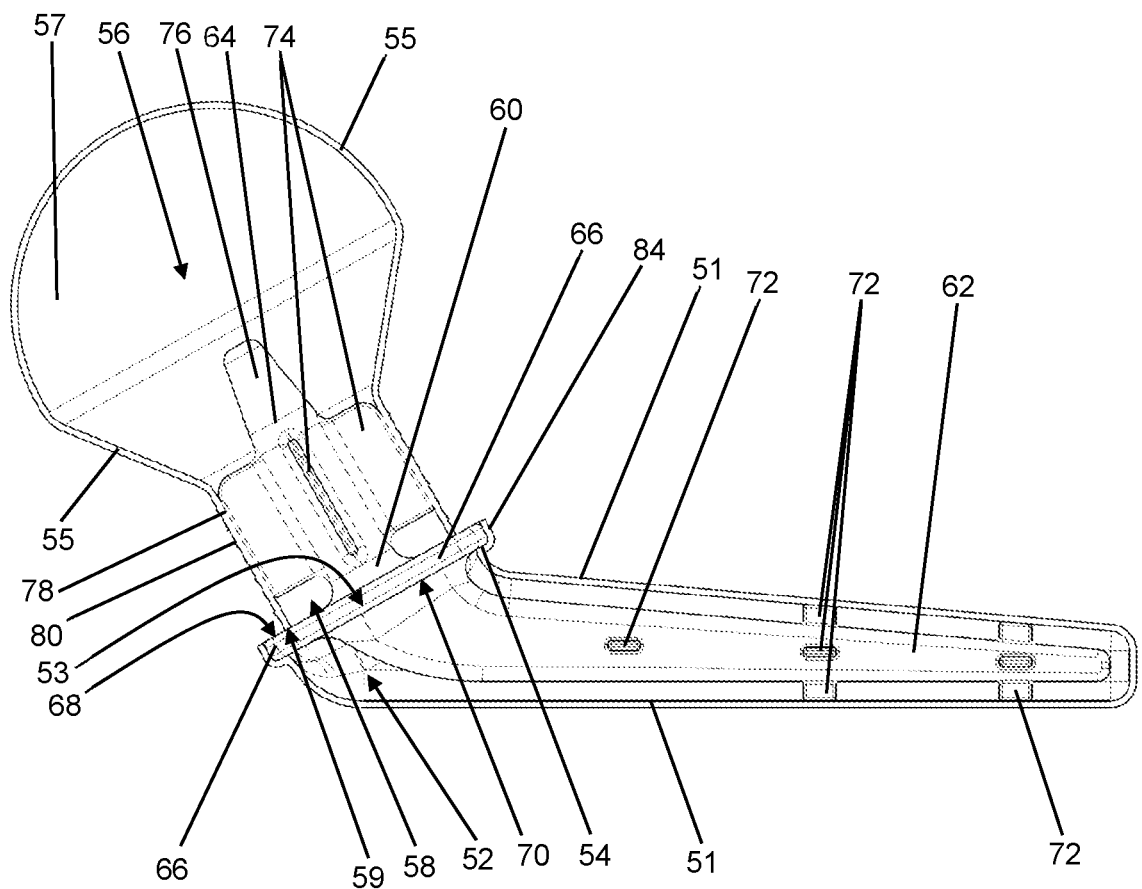
FIG. 10 shows a partial cross-sectional view of the assembled second device according to the invention.

FIGS. 1 to 7 are drawings showing various views of a first exemplary embodiment of a device according to the invention for producing a hip joint spacer, as shown in FIG. 7, and parts of the device.

The first device according to the invention is suitable and provided for producing a spacer 38 (see FIG. 7) for a hip joint. The device has a stem mold 1 and a head mold 5 and a metal core 10. The stem mold 1 and the head mold 5 are preferably in each case of one-part construction. The stem mold 1 and the head mold 5 may together form a two-part casting mold for shaping a bone cement paste 36 introduced therein (see FIG. 6). The bone cement paste 36 may to this end cure in the casting mold. FIGS. 1, 3, 5 and 6 show the stem mold 1 and the head mold 5 sectioned, such that the interior structure of the device is visible. The metal core 10 is shown sectioned only in FIG. 6 and otherwise unsectioned.

The stem mold 1 may have an inner space 2 in which the bone cement paste 36 is shapeable to form a stem 42 of the spacer 38. The inner space 2 may be accessible via a proximal opening 3, such that the bone cement paste 36 is introducible through the proximal opening 3 of the stem mold 1 into the inner space 2 and the metal core 10 is able to be partially pushed in through the proximal opening 3 into the inner space 2 of the stem mold 1. Around the proximal opening 3, the stem mold 1 may have a proximal wall 4 which delimits and encloses the proximal opening 3.

The head mold 5 may have a hollow space 6 in which the bone cement paste 36 is shapeable to form a head 40 of the spacer 38. On a proximal side of the hollow space 6, the hollow space 6 may have a spherical surface-shaped inner surface 7 which serves to form the actual joint surface of the spacer 38. The spherical surface-shaped inner surface 7 of the hollow space 6 accordingly shapes the hip joint surface of the spacer 38, which surface is intended to slide in a hip socket. The hollow space 6 may be accessible via a distal opening 8, such that the bone cement paste 36 is introducible through the distal opening 8 of the head mold 5 into the hollow space 6 and the metal core 10 can be partially pushed in through the distal opening 8 into the hollow space 6 of the head mold 5. Around the distal opening 8, the head mold 5 may have a distal wall 9 which delimits and encloses the distal opening 8.

Figure 14:
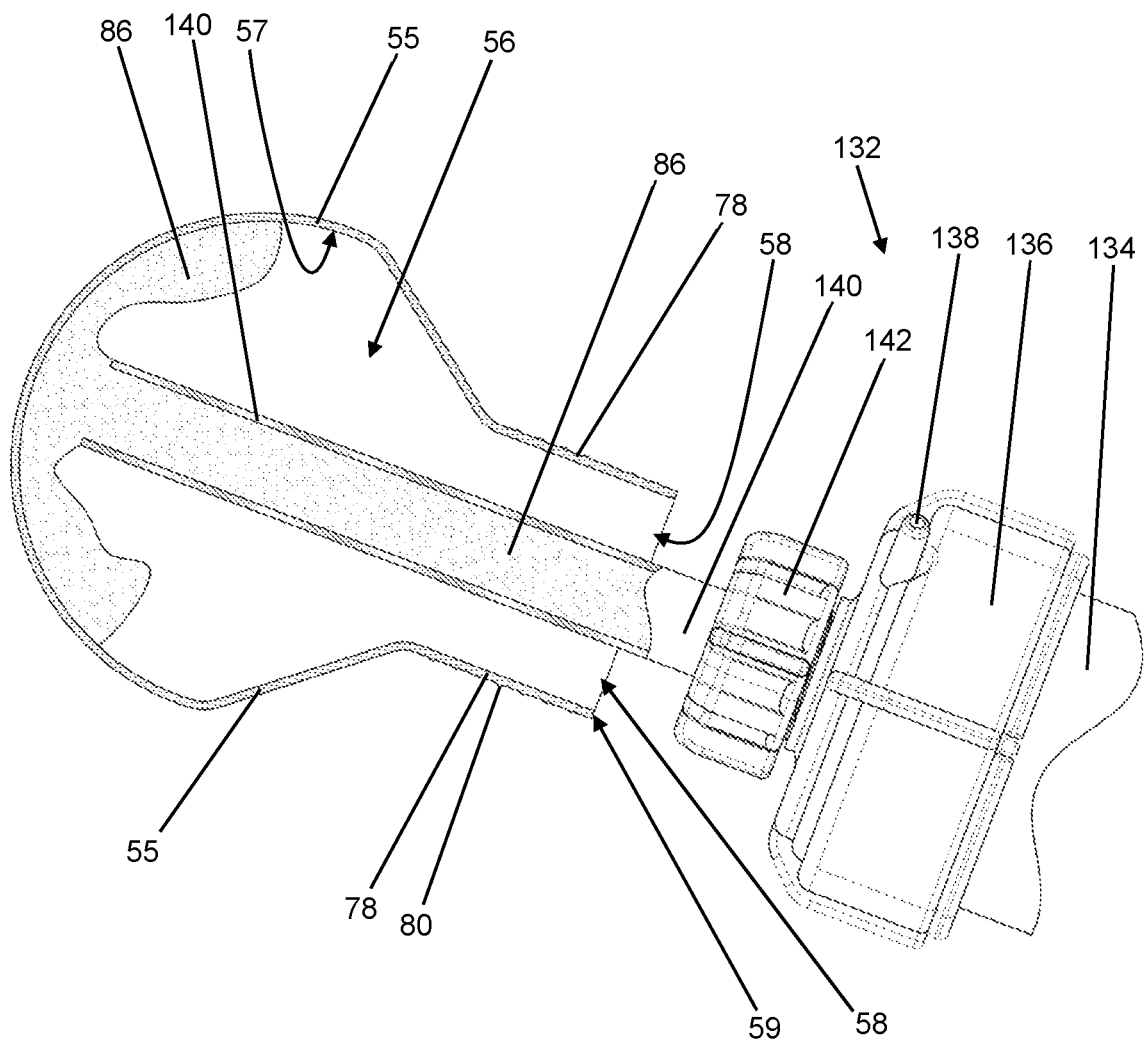
FIG. 14 shows a partial cross-sectional view of the third device according to the invention during introduction of a bone cement paste for producing the spacer.
Figure 15:
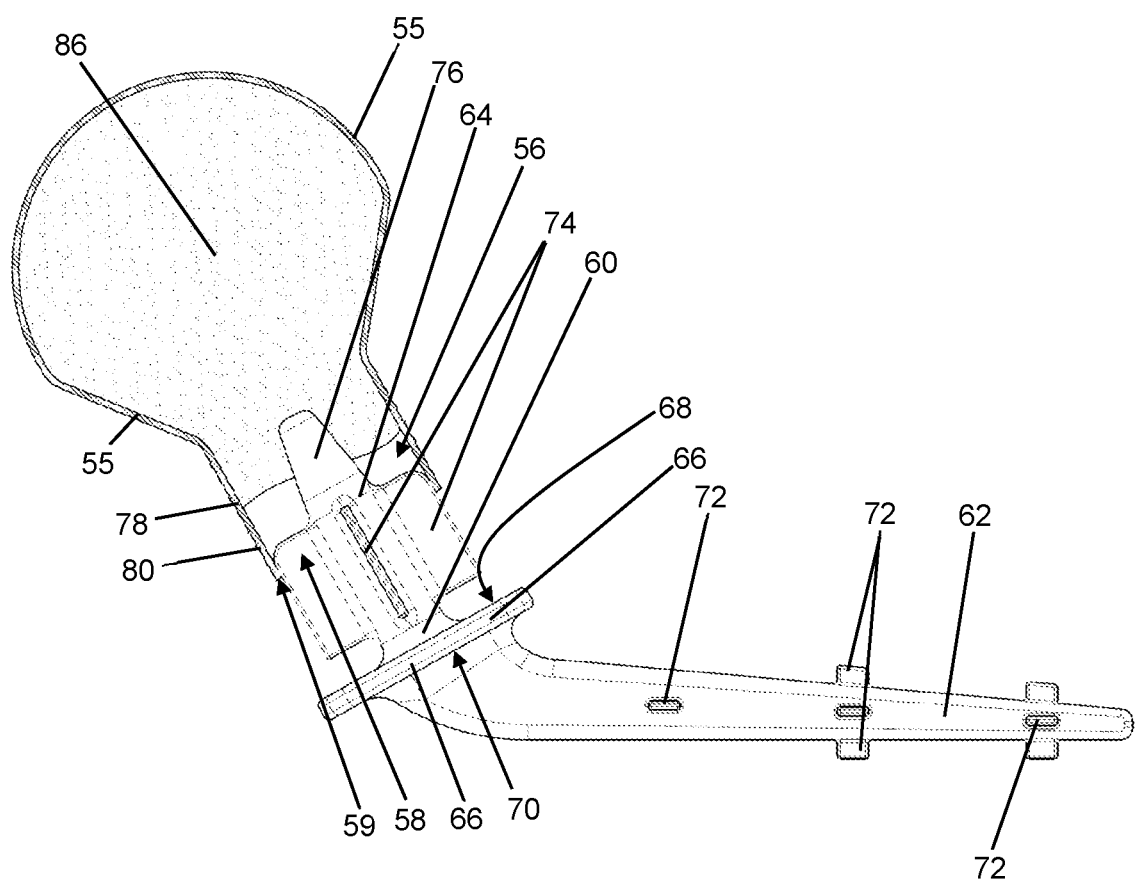
FIG. 15 shows a partial cross-sectional view of the second device according to the invention while the metal core is being pushed into the head mold filled with bone cement paste for producing the spacer.
Figure 16:
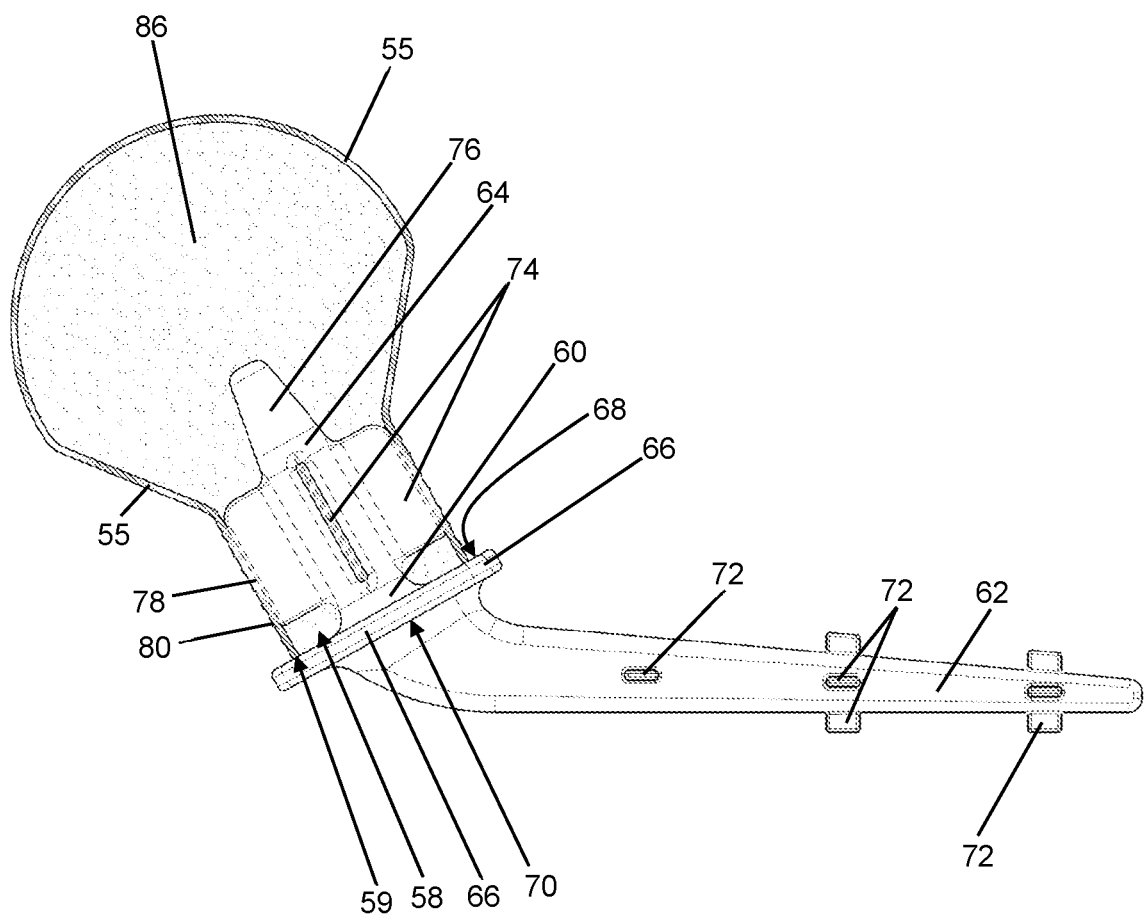
FIG. 16 shows a partial cross-sectional view of the second device according to the invention with the metal core pushed completely to the limit stop into the head mold filled with bone cement paste for producing the spacer.
Figure 17:
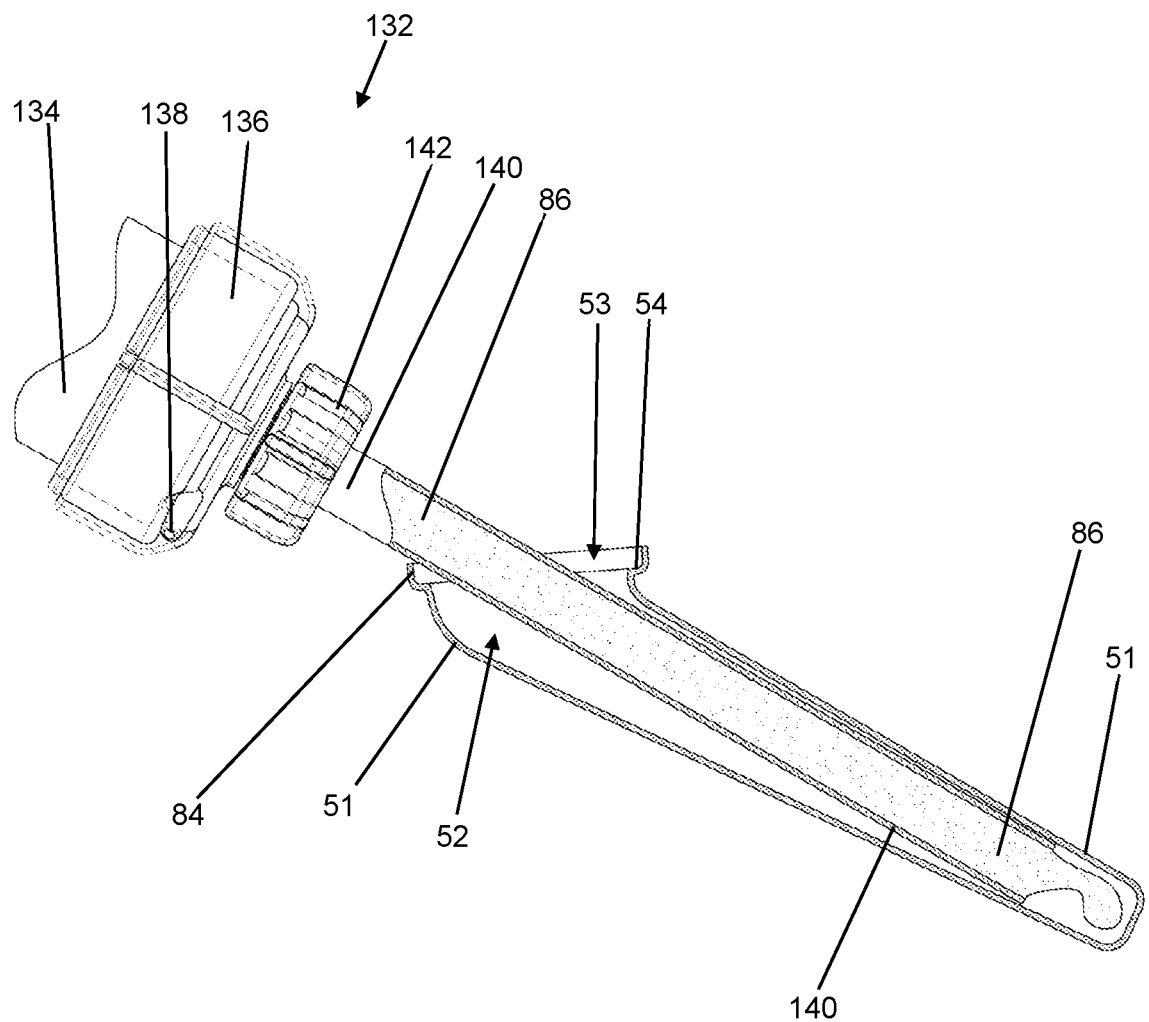
FIG. 17 shows a partial cross-sectional view of the second device according to the invention during introduction of a bone cement paste for producing the spacer.
Figure 18:
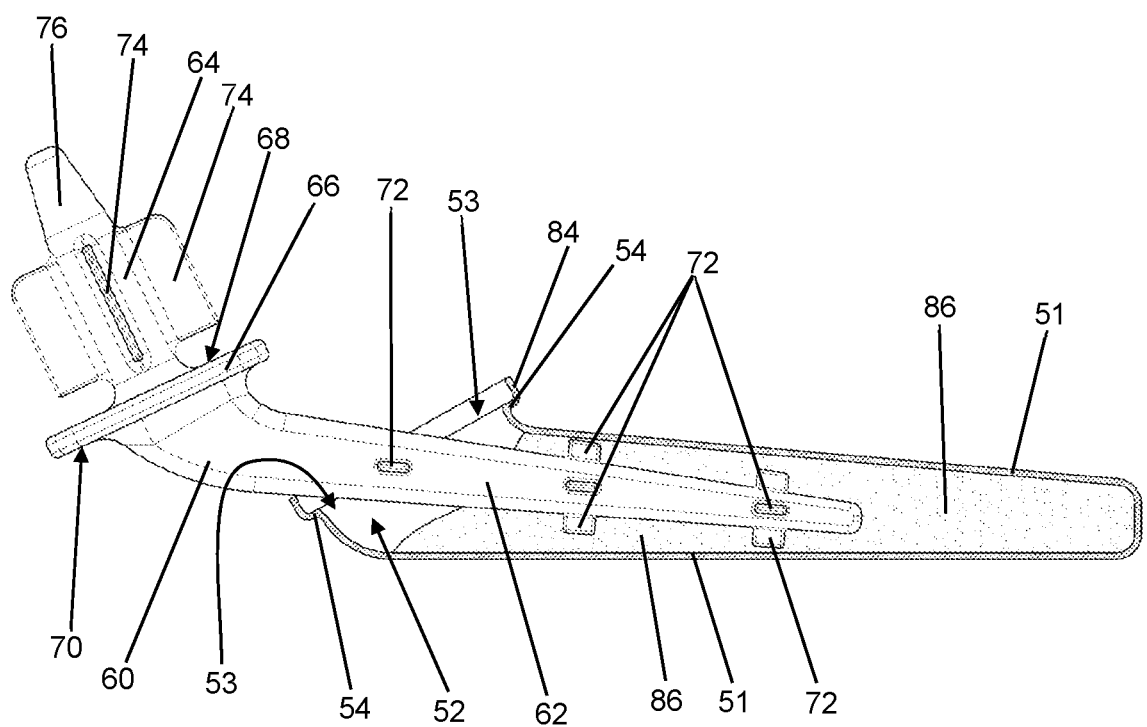
FIG. 18 shows a partial cross-sectional view of the second device according to the invention while the metal core is being pushed into the stem mold filled with bone cement paste for producing the spacer.
Figure 19:
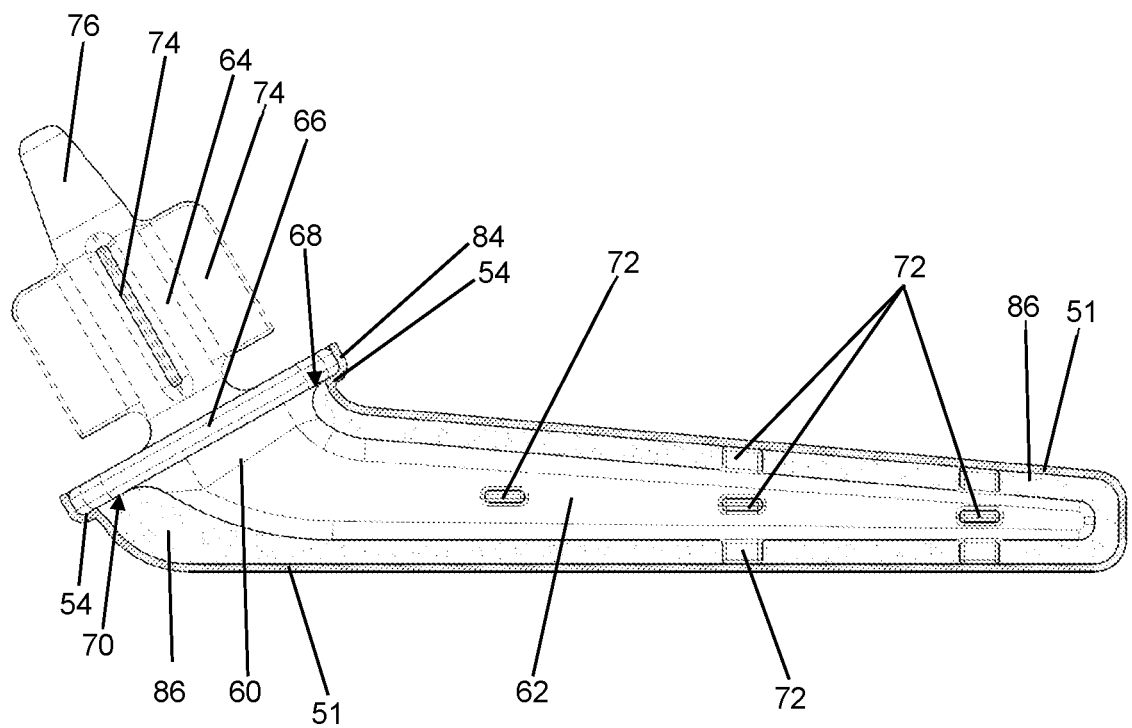
FIG. 19 shows a partial cross-sectional view of the second device according to the invention with the metal core pushed completely to the limit stop into the stem mold filled with bone cement paste for producing the spacer.

Before being introduced, the bone cement paste 36 may have been mixed from a monomer liquid and a cement powder (not shown), wherein at least one antibiotic and/or at least one antimycotic may preferably also be admixed with the bone cement paste 36. The bone cement paste 36 can be filled into the stem mold 1 and into the head mold 5 via a bone cement applicator 132, as shown in FIGS. 14 and 17 relating to the second exemplary embodiment.

The metal core 10 may consist of a biocompatible metal, such as for example stainless steel or titanium. The metal core 10 serves to reinforce and thus mechanically stabilize the spacer 38. The metal core 10 has a stem part 12, a head part 14 and a flange 16, which is arranged between the stem part 12 and the head part 14. The metal core 10 is preferably one-part. The stem part 12 and the head part 14 may be connected together via the flange 16. The flange 16 may project out in the radial direction from the axes of the head part 14 and the stem part 12. The protruding flange 16 has a proximal surface 18 and an opposing distal surface 20.

The proximal wall 4 of the stem mold 1 may be shaped to match the distal surface 20 of the flange 16, such that the stem mold 1 is placeable at least in places flush against the distal surface 20 of the flange 16. This permits definite positioning of the stem mold 1 on the flange 16 of the metal core 10. Similarly, the distal wall 9 of the head mold 5 may be shaped to match the proximal surface 18 of the flange 16, such that the head mold 5 is placeable at least in places flush against the proximal surface 18 of the flange 16. This permits definite positioning of the head mold 5 on the flange 16 of the metal core 10.

A plurality of protruding spacing pieces 22 of an elongate shape may be arranged on the stem part 12, which spacing pieces facilitate positioning and orientation of the stem part 12 in the stem mold 1 when the stem part 12 is pushed through the proximal opening 3 into the stem mold 1. The height of the spacing pieces 22 is here selected such that they rest against the inner wall of the inner space 2 of the stem mold 1 when the stem part 12 is completely pushed into the stem mold 1. The limit stop for this purpose may be formed by the proximal wall 4 of the stem mold 1 and by the distal surface 20 of the flange 16.

A plurality of protruding centering means 24, for example in the form of four projecting fins, may be arranged on the head part 14, which centering means facilitate positioning and orientation of the head part 14 in the head mold 5 when the head part 14 is pushed through the distal opening 8 into the head mold 5. For the same purpose, the head part 14 may be shaped on the proximal side thereof with a cone 26 which is intended to facilitate its being pushed into the bone cement paste 36. The orientation of the fins is preferably selected such that they can slide along the linear surfaces thereof into the hollow space 6 of the head mold 5. The head mold 5 may have a neck mold 28 with a cylindrical inner space as part of the hollow space 6. The centering means 24 can slide on the inner wall of the neck mold 28. The height of the centering means 24 is preferably here selected such that they rest against the inner wall of the hollow space 6 of the neck mold 28 of the head mold 5 when the head part 14 is completely pushed into the head mold 5. The limit stop for this purpose may be formed by the distal wall 9 of the head mold 5 and by the proximal surface 18 of the flange 16.

The neck mold 28 may have a plurality of projecting rings 30 in the form of peripheral thickened portions along which the neck mold 28 can be cut and so shortened. The rings 30 may to this end be uniformly spaced, in particular in a uniform integral or half-integral centimeter or inch spacing. In this way, the length of a neck 44 of the spacer 38 to be produced, which is determined by the length of the neck mold 28, can be adjusted.

The flange 16 may have a plurality of protrusions 32 which may project out in a radial or transverse direction from the metal core 16. The protrusions 32 may form the proximal surface 18 and/or the distal surface 20 of the flange 16 or be part of the proximal surface 18 and/or distal surface 20 of the flange 16. Excess bone cement paste 36 may emerge from the stem mold 1 and theoretically also from the head mold 5 between the interspaces between the projections 32 when the metal core 10 is pushed in.

A collar 34 may be formed on the stem mold 1, which collar, starting from the proximal wall 4 of the stem mold 1, surrounds the flange 16.

According to the invention, the stem mold 1 and the head mold 5 can be inexpensively produced from plastics material by injection molding or can even also be produced from a thermoformed plastics film since, even during introduction of a high-viscosity bone cement paste, they do not have to withstand any very large forces. This is possible because according to the invention the bone cement paste 36 is introduced into the stem mold 1 and the head mold 5 as the casting mold without the metal core 10 already being arranged therein and consequently having to be flowed around. Arranging the metal core 10 in the stem mold 1 and in the head mold 5 subsequent to the introduction of the bone cement paste 36 is possible because the stem mold 1 and the head mold 5 are placed against the flange 16 of the metal core 10 and can accordingly be arranged and oriented to fit with the metal core 10 and with one another. As a result, there is no need for the stem mold 1 and the head mold 5 to be screwed or fastened together in a costly, pressure-absorbing and stable manner.

Once the bone cement paste 36 in the casting mold assembled from the stem mold 1 and the head mold 5 over the metal core 10 has cured, a bone cement paste 36 contained therein may cure (see FIG. 6). The resultant spacer 38 can subsequently be demolded by pulling off the stem mold 1 and separating and detaching the head mold 5. The spacer 38, as shown in FIG. 7, is left behind, wherein the metal core 10 is enclosed or largely enclosed in the spacer 38 as reinforcement. The flange 16 or the protrusions 32 of the flange 16 at the transition from the stem 42 to the neck 44 of the spacer 38 are still apparent on the surface of the spacer 38. The outer surfaces of the spacing pieces 22 in the stem 42 and the centering means 24 in the neck 44 of the spacer 38 may likewise also be apparent.

Figure 11:
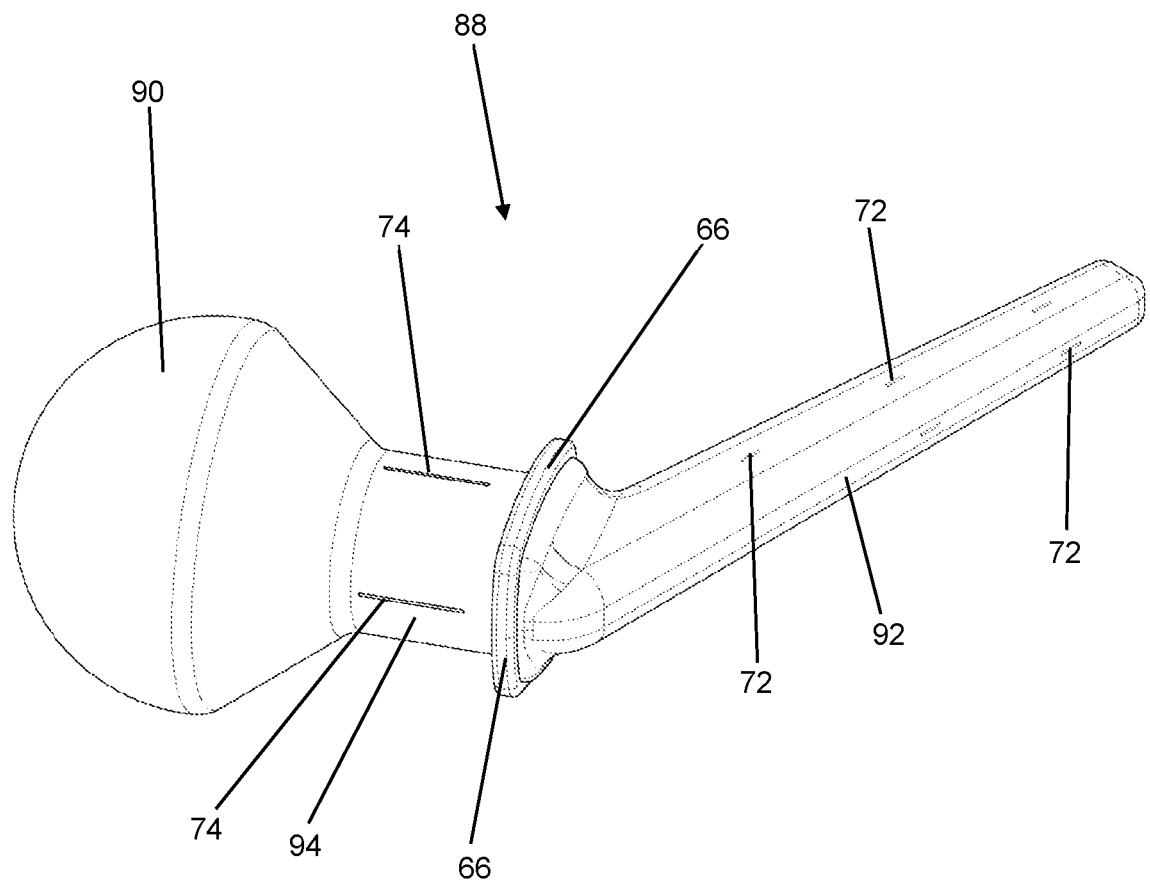
FIG. 11 shows a perspective view of a hip spacer produced with the second device according to the invention.

FIGS. 8 to 12 and 14 to 20 are drawings showing various views of a second exemplary embodiment of a device according to the invention for producing a hip joint spacer, as shown in FIG. 11, and parts of the device. FIG. 13 shows a third exemplary embodiment which is distinguished from the second exemplary embodiment merely by a different diameter for shaping the joint head but is otherwise identical.

The second device according to the invention and the third device according to the invention are suitable and provided for producing a spacer 88 (see FIG. 11) for a hip joint. The second device according to the invention has a stem mold 51 and a head mold 55 and a metal core 60. The stem mold 51 and the head mold 55 are preferably in each case of one-part construction. The stem mold 51 and the head mold 55 may together form a two-part casting mold for shaping a bone cement paste 86 introduced therein (see FIGS. 14 to 20). The bone cement paste 86 may to this end cure in the casting mold. FIGS. 8, 10, 12 and 14 to 20 show the stem mold 51 and the head mold 55 sectioned, such that the interior structure of the device is visible. The metal core 60 is always shown unsectioned.

The stem mold 51 may have an inner space 52 in which the bone cement paste 86 is shapeable to form a stem 92 of the spacer 88. The inner space 52 may be accessible via a proximal opening 53, such that the bone cement paste 86 is introducible through the proximal opening 53 of the stem mold 51 into the inner space 52 and the metal core 60 is able to be partially pushed in through the proximal opening 53 into the inner space 52 of the stem mold 51. Around the proximal opening 53, the stem mold 51 may have a proximal wall 54 which delimits and encloses the proximal opening 53.

The head mold 55 may have a hollow space 56 in which the bone cement paste 86 is shapeable to form a head 90 of the spacer 88. On a proximal side of the hollow space 56, the hollow space 56 may have a spherical surface-shaped inner surface 57 which serves to form the actual joint surface of the spacer 88. The spherical surface-shaped inner surface 57 of the hollow space 56 accordingly shapes the hip joint surface of the spacer 88, which surface is intended to slide in a hip socket. The hollow space 56 may be accessible via a distal opening 58, such that the bone cement paste 86 is introducible through the distal opening 58 of the head mold 55 into the hollow space 56 and the metal core 60 is able to be partially pushed in through the distal opening 58 into the hollow space 56 of the head mold 55. Around the distal opening 58, the head mold 55 may have a distal wall 59 which delimits and encloses the distal opening 58.

The metal core 60 may consist of a biocompatible metal, such as for example stainless steel or titanium. The metal core 60 serves to reinforce and thus mechanically stabilize the spacer 88. The metal core 60 has a stem part 62, a head part 64 and a flange 66, which is arranged between the stem part 62 and the head part 64. The metal core 60 is preferably one-part. The stem part 62 and the head part 64 may be connected together via the flange 66. The flange 66 may project out in the radial direction from the axes of the head part 64 and the stem part 62. The protruding flange 66 has a proximal surface 68 and an opposing distal surface 70.

The proximal wall 54 of the stem mold 51 may be shaped to match the distal surface 70 of the flange 66, such that the stem mold 51 is placeable at least in places flush against the distal surface 70 of the flange 66. This permits definite positioning of the stem mold 51 on the flange 66 of the metal core 60. Similarly, the distal wall 59 of the head mold 55 may be shaped to match the proximal surface 68 of the flange 66, such that the head mold 55 is placeable at least in places flush against the proximal surface 68 of the flange 66. This permits definite positioning of the head mold 55 on the flange 66 of the metal core 60.

A plurality of protruding spacing pieces 72 of an elongate shape may be arranged on the stem part 62, which spacing pieces facilitate positioning and orientation of the stem part 62 in the stem mold 51 when the stem part 62 is pushed through the proximal opening 53 into the stem mold 51. The height of the spacing pieces 72 is here selected such that they rest against the inner wall of the inner space 52 of the stem mold 51 when the stem part 62 is completely pushed into the stem mold 51. The limit stop for this purpose may be formed by the proximal wall 54 of the stem mold 51 and by the distal surface 70 of the flange 66.

A plurality of protruding centering means 74, for example in the form of four projecting fins, may be arranged on the head part 64, which centering means facilitate positioning and orientation of the head part 64 in the head mold 55 when the head part 64 is pushed through the distal opening 58 into the head mold 55. For the same purpose, the head part 64 may be shaped on the proximal side thereof with a cone 76 which is intended to facilitate its being pushed into the bone cement paste 86. The orientation of the fins is preferably selected such that they can slide along the linear surfaces thereof into the hollow space 56 of the head mold 55. The head mold 55 may have a neck mold 78 with a cylindrical inner space as part of the hollow space 56. The centering means 74 can slide on the inner wall of the neck mold 78. The height of the centering means 74 is preferably here selected such that they rest against the inner wall of the hollow space 56 of the neck mold 78 of the head mold 55 when the head part 64 is completely pushed into the head mold 55. The limit stop for this purpose may be formed by the distal wall 59 of the head mold 55 and by the proximal surface 68 of the flange 66.

The neck mold 78 may have a plurality of projecting rings 80 in the form of peripheral thickened portions along which the neck mold 78 can be cut and so shortened. The rings 80 may to this end be uniformly spaced, in particular in a uniform integral or half-integral centimeter or inch spacing. In this way, the length of a neck 94 of the spacer 88 to be produced, which is determined by the length of the neck mold 78, can be adjusted.

A collar 84 may be formed on the stem mold 51, which collar, starting from the proximal wall 54 of the stem mold 51, surrounds the flange 66.

According to the invention, the stem mold 51 and the head mold 55 can be inexpensively produced from plastics material by injection molding or can even also be produced from a thermoformed plastics film since, even during introduction of a high-viscosity bone cement paste, they do not have to withstand any very large forces. This is possible because according to the invention the bone cement paste 86 is introduced into the stem mold 51 and the head mold 55 as the casting mold without the metal core 60 already being arranged therein and consequently having to be flowed around. Arranging the metal core 60 in the stem mold 51 and in the head mold 55 subsequent to the introduction of the bone cement paste 86 is possible because the stem mold 51 and the head mold 55 are placed against the flange 66 of the metal core 60 and can accordingly be arranged and oriented to fit with the metal core 60 and with one another. As a result, there is no need for the stem mold 51 and the head mold 55 to be screwed or fastened together in a costly, pressure-absorbing and stable manner.

Figure 20:
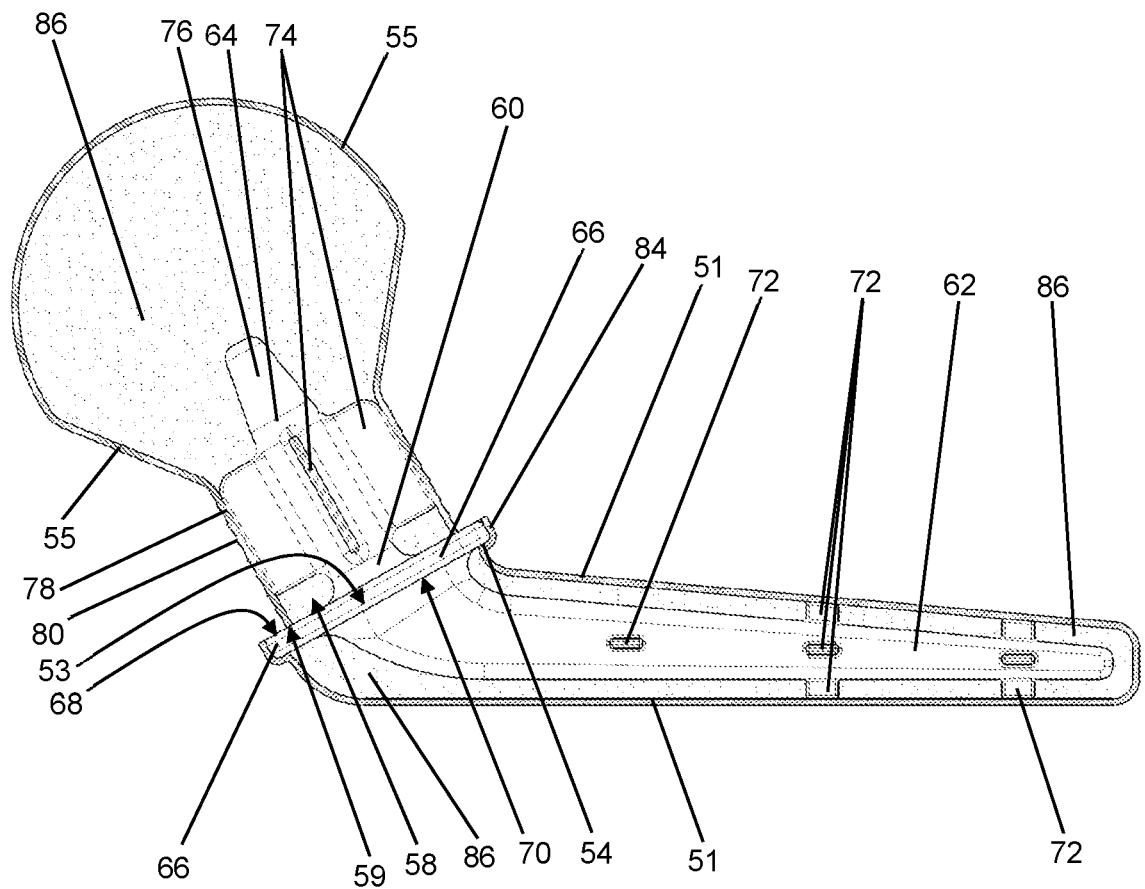
FIG. 20 shows a partial cross-sectional view of the assembled second device according to the invention filled with bone cement paste during curing of the bone cement paste.

Once the bone cement paste 86 in the casting mold assembled from the stem mold 51 and the head mold 55 over the metal core 60 has cured, a bone cement paste 86 contained therein may cure (see FIG. 20). The resultant spacer 38 can subsequently be demolded by pulling off the stem mold 51 and separating and detaching the head mold 55. The spacer 88, as shown in FIG. 11, is left behind, wherein the metal core 60 is enclosed or largely enclosed in the spacer 88 as reinforcement. The flange 66 at the transition from the stem 92 to the neck 94 of the spacer 88 is still apparent on the surface of the spacer 88. The outer surfaces of the spacing pieces 72 in the stem 92 and the centering means 74 in the neck 94 of the spacer 88 may likewise also be apparent.

Before being introduced into the stem mold 51 or into the head mold 55, the bone cement paste 86 may have been mixed from a monomer liquid and a cement powder (not shown), wherein at least one antibiotic and/or at least one antimycotic may preferably also be admixed with the bone cement paste 86. The bone cement paste 86 may be filled into the stem mold 51 and into the head mold 55 via a bone cement applicator 132 (see FIGS. 14 and 17). The inner space 52 of the stem mold 51 is here filled from the distal side and the hollow space 56 of the head mold 55 from the proximal side in order to prevent entrapped air. Vent openings (not shown) may also be provided in the walls of the stem mold 51 and the head mold 52 to avoid entrapped air.

Once the bone cement paste 86 has been filled to excess into the stem mold 51 and the head mold 55, the stem part 62 of the metal core 60 can be pushed into the stem mold 51 and the head part 64 of the metal core 60 pushed into the head mold 55. The flange 66 forms the limit stop for both. Any emerging excess bone cement paste 86 can be removed. The bone cement paste 86 cures in this state with the metal core 60 enclosed therein (see FIG. 20).

Figure 12:
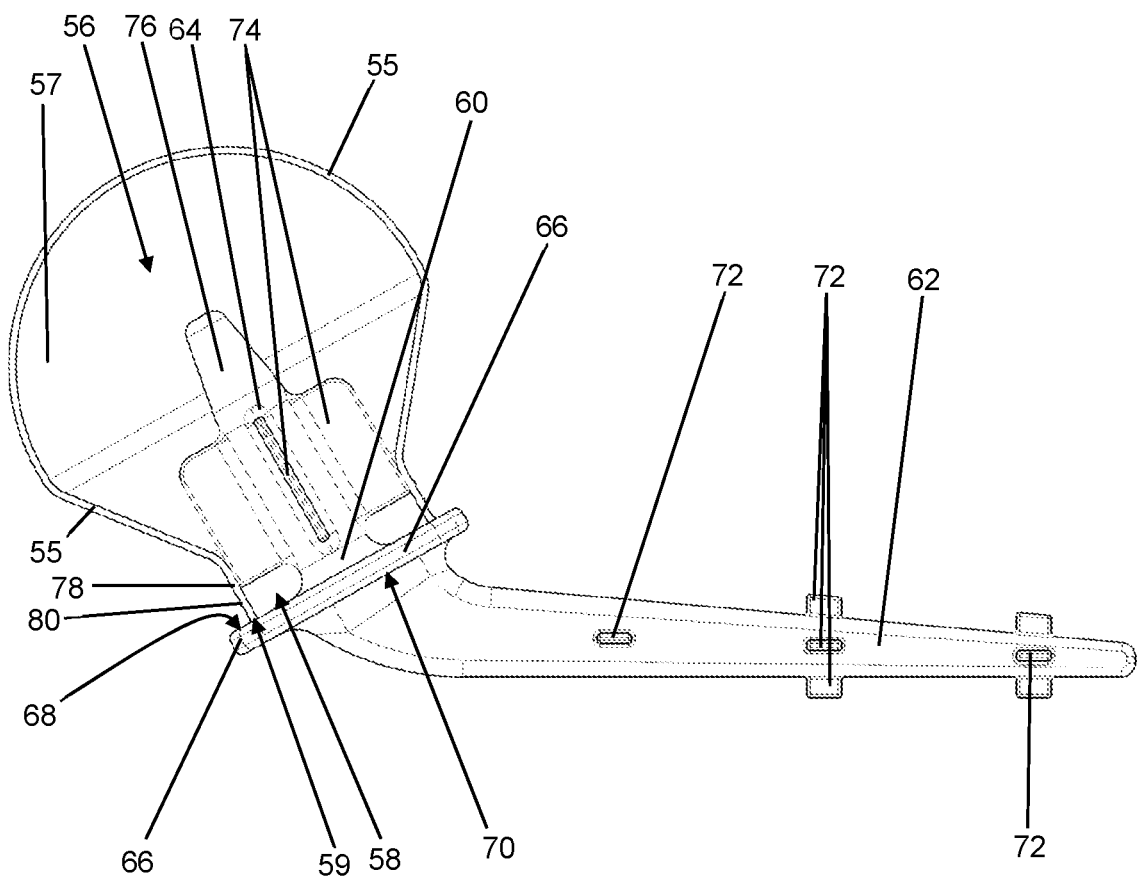
FIG. 12 shows a partial cross-sectional view of the assembled second device according to the invention with shortened neck mold.
Figure 13:
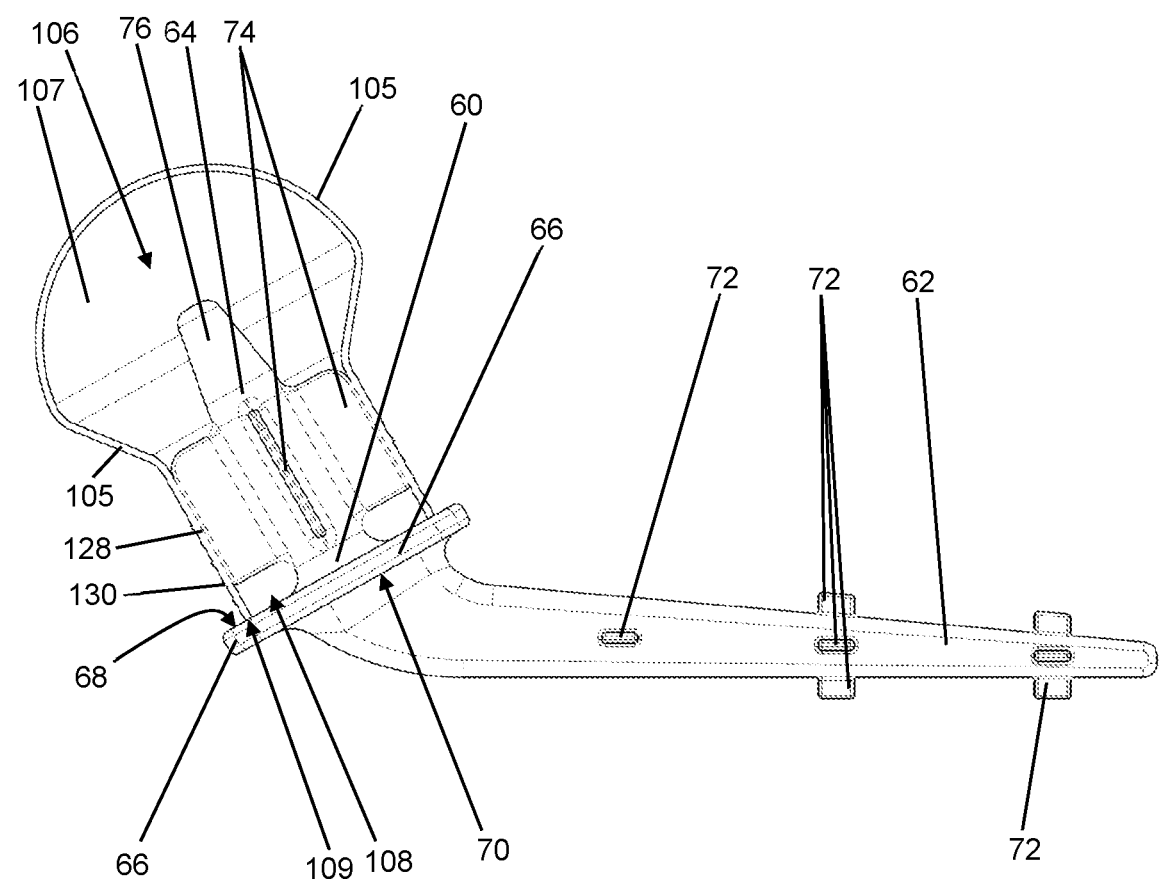
FIG. 13 shows a partial cross-sectional view of an assembled third device according to the invention with a smaller head mold.

In order to adapt the spacer 88 to anatomical circumstances, the neck 78 can be shortened along the rings 80, as shown in FIG. 12.

The third exemplary embodiment shown in FIG. 13 differs from the second exemplary embodiment merely in that it has a different head mold 105 with a different radius of a spherical surface-shaped inner surface 107. Due to the different shape of the head mold 105, a different hollow space 106 is also present in the head mold 105. Similarly to the head mold 55, the head mold 105 may have a distal opening 108 and a circumferential distal wall 109. A neck mold 128 with peripheral rings 130 may likewise be provided. All the other parts of the third exemplary embodiment are identical to the second exemplary embodiment. Together with the head mold 55 and the metal core 60 and the stem mold 51 and, if desired also with the bone cement applicator 132, the head mold 105 may take the form of a set according to the invention.

The bone cement applicator 132 may have a cartridge 134 for mixing the bone cement paste 86, which cartridge may, apart from an opening, be closed on the front side by a cartridge head 136. In addition, a vacuum port 138 may be arranged on the cartridge head 136, such that the bone cement paste 86 can mixed under a vacuum in the interior of the cartridge 134. Once completely mixed, the bone cement paste 86 can be pressed through the opening and through a delivery tube 140 into the stem mold 51 and into the head mold 55 (see FIGS. 14 and 17). A static mixer (not shown) may be arranged in the delivery tube 140 with which the starting components of the bone cement paste 86 can be intermixed. The delivery tube 140 can be fastened with a sleeve nut 142 to the cartridge head 136.

FIGS. 21 to 23 and 24A), 24B), 25A) and 25B) are drawings showing various views of a set according to the invention and of a fourth exemplary embodiment of a device according to the invention for producing a hip joint spacer, as shown in FIGS. 25A) and 25B), and parts of the device. Similarly to the combination of the different head molds of the second and third exemplary embodiment, the set has two differently shaped head molds 155, 205. FIGS. 24C) to 24H) and 25C) to 25H) show alternatives with shortened and unshortened head molds 255 with spherical surface-shaped inner surfaces 257 with different radii.

Figure 21:
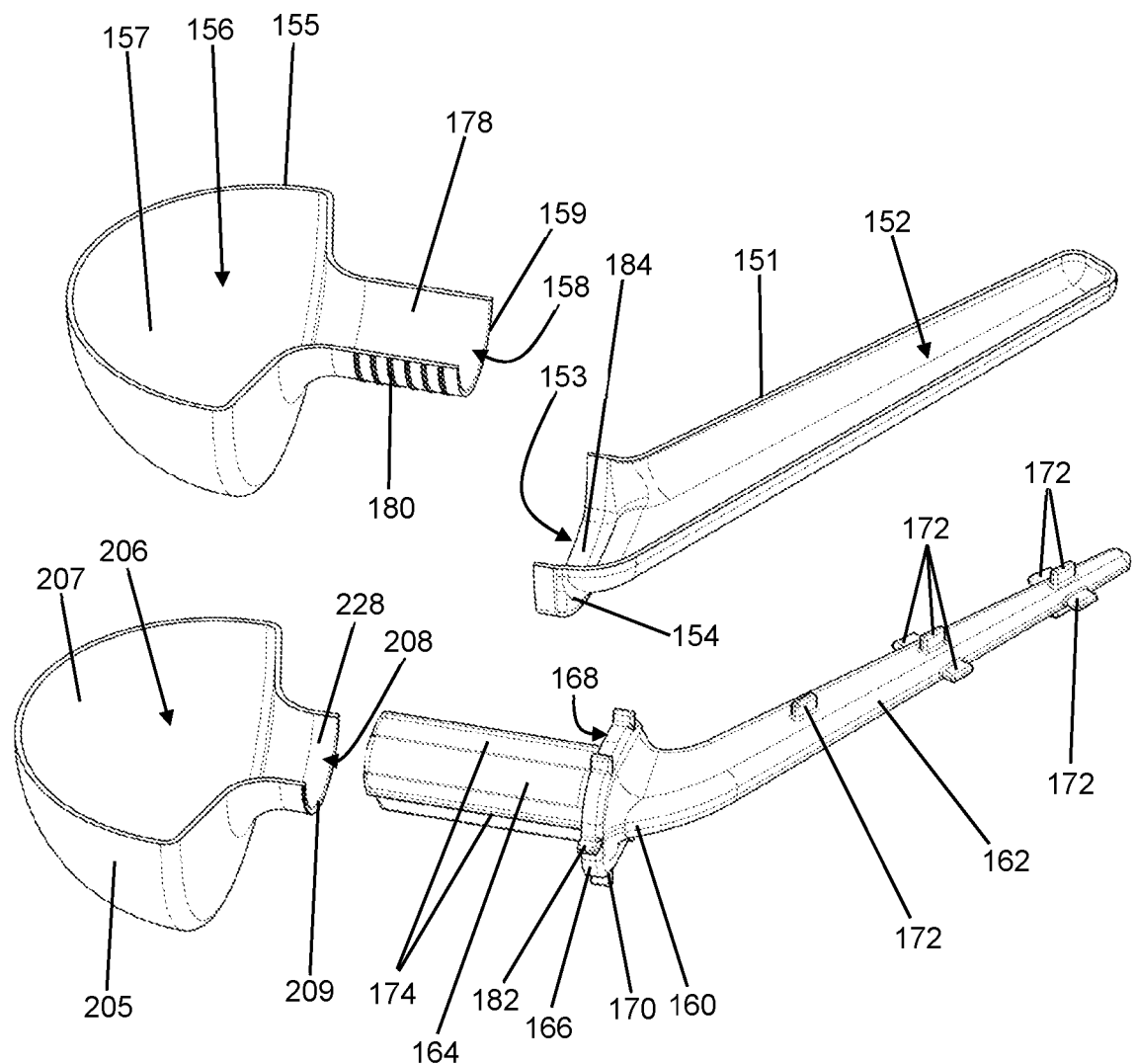
FIG. 21 shows a perspective partial cross-sectional view of the parts of a first set according to the invention with an exemplary fourth device according to the invention with two different head molds for producing a hip joint spacer.
Figure 22:
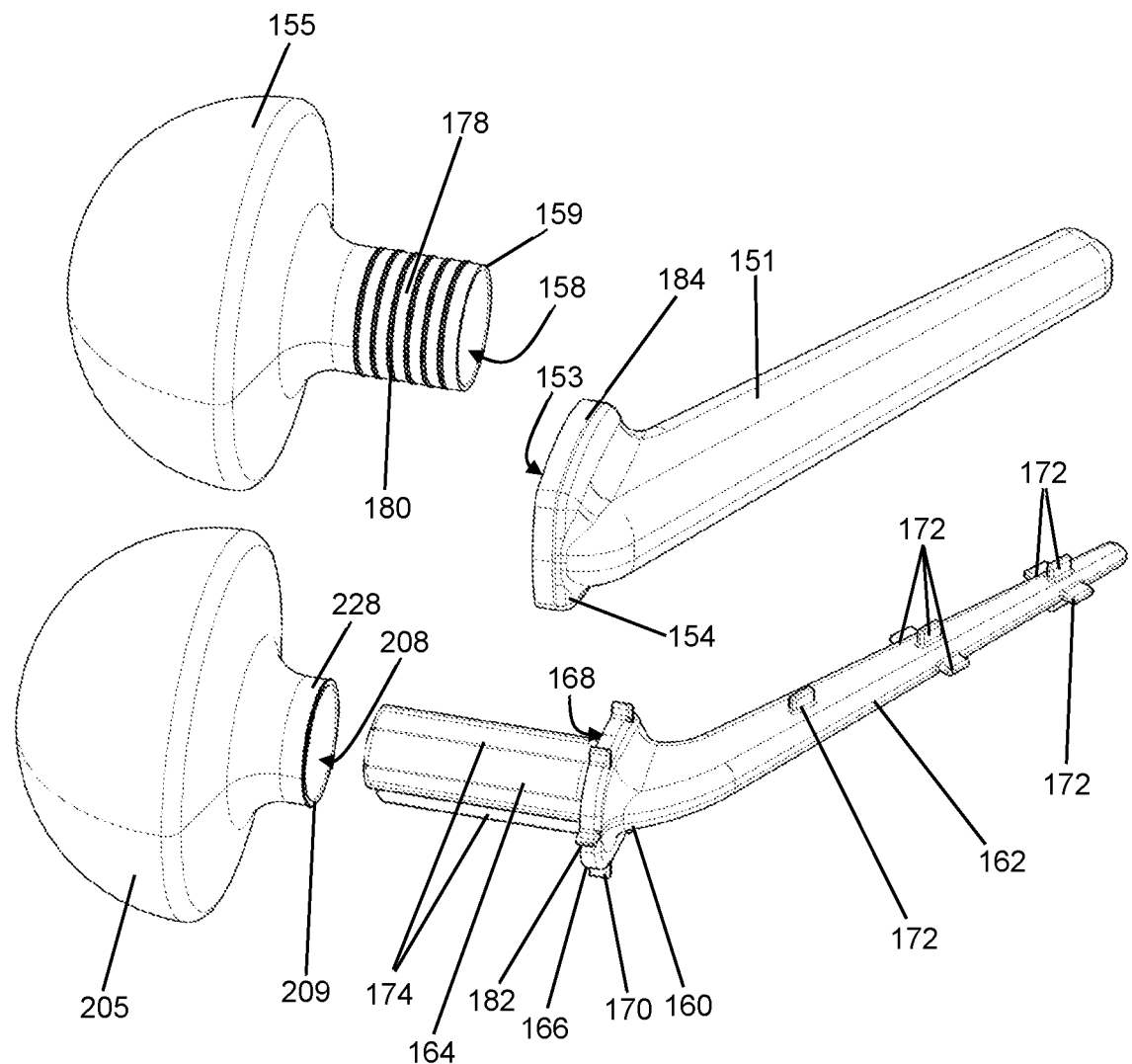
FIG. 22 shows a perspective external view of the parts of the first device according to the invention according to FIG. 21.
Figure 23:
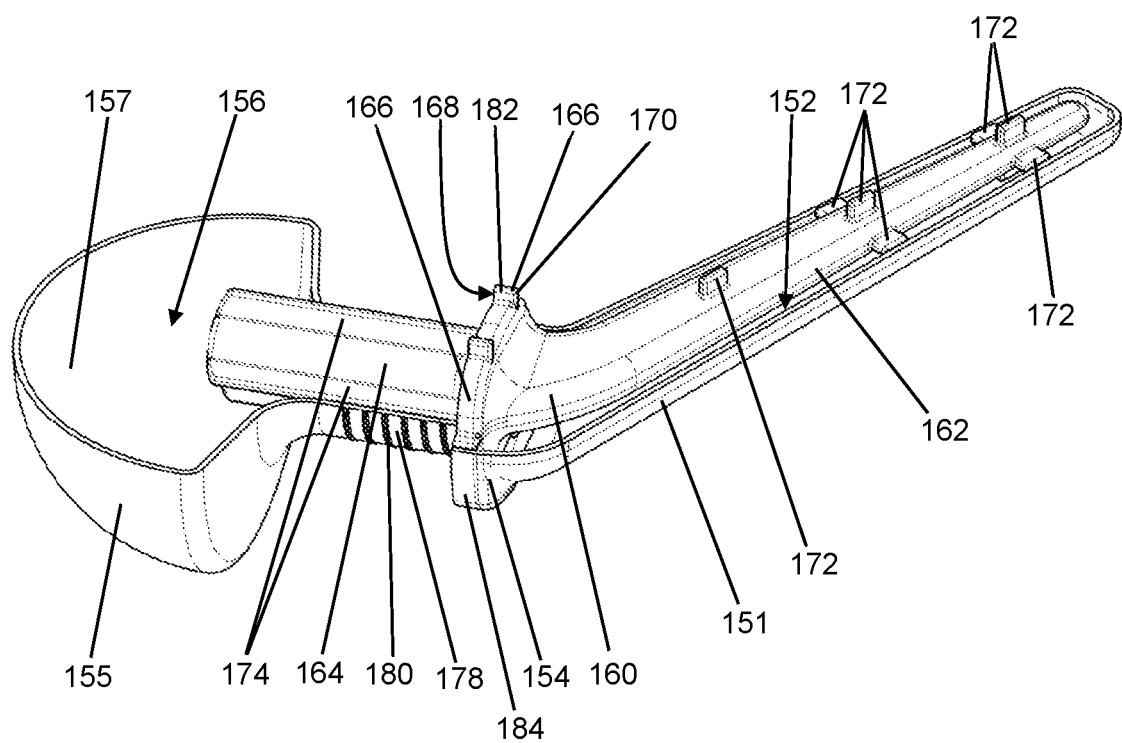
FIG. 23 shows a schematic perspective partial cross-sectional view of the assembled fourth device according to the invention of the first set according to the invention according to FIGS. 21 and 22.
Figure 24:
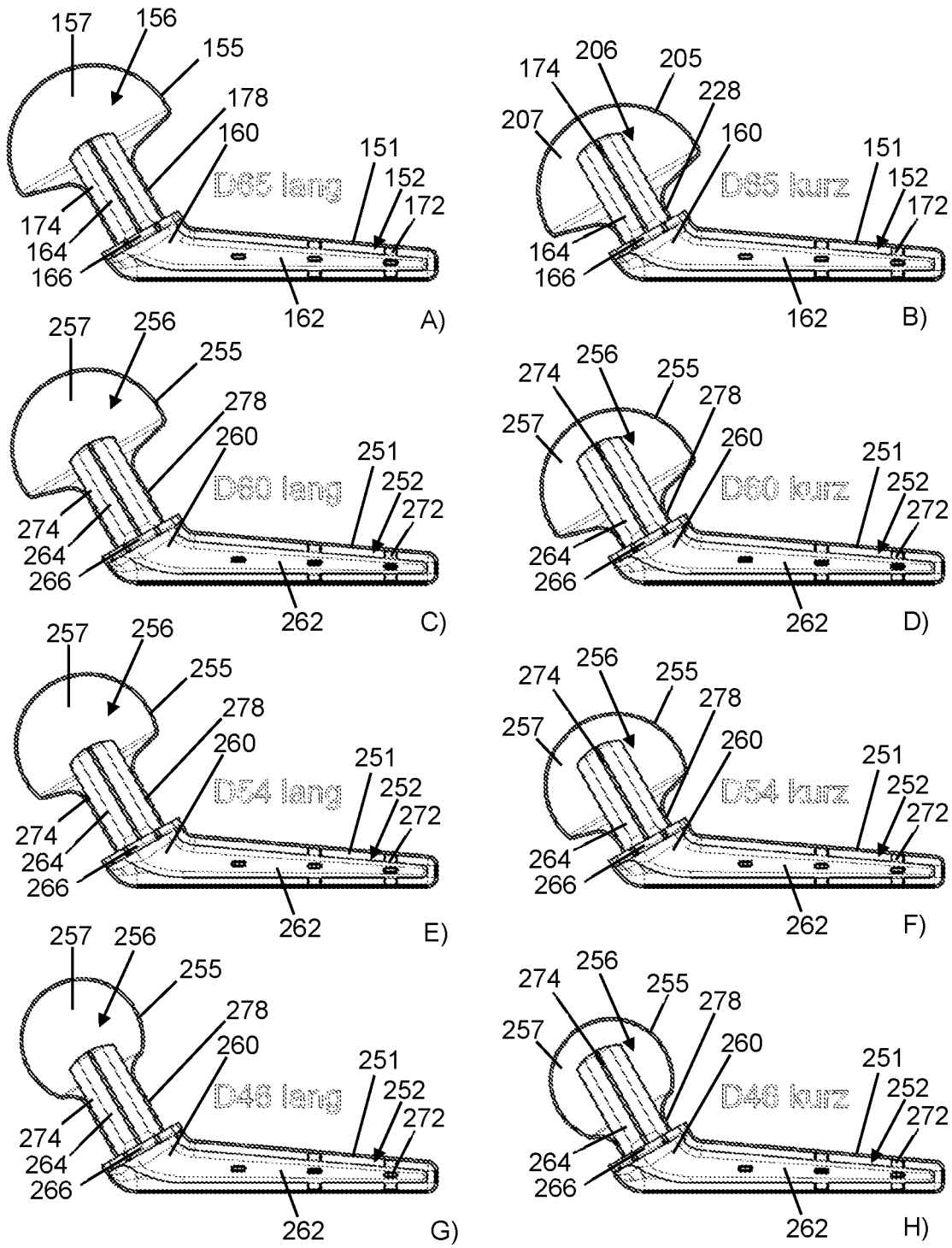

The set or the fourth device according to the invention is suitable and provided for producing two differently shaped spacers 188, 238 (see FIGS. 25A) and 25B)) for a hip joint. The device has a stem mold 151 and two head molds 155, 205 and a metal core 160. The stem mold 151 and the head molds 155, 205 are preferably in each case of one-part construction. The stem mold 151 and the head molds 155, 205 may together form two two-part casting molds for shaping a bone cement paste introduced therein (not shown but similar to FIGS. 6 and 20). The bone cement paste may to this end cure in the casting mold. FIGS. 21, 23 and 24 show the stem mold 151 and the head molds 155, 205 sectioned, such that the interior structure of the device is visible. The metal core 160 is always shown unsectioned.

The stem mold 151 may have an inner space 152 in which the bone cement paste is shapeable to form a stem 192, 242 of the spacer 188, 238. The inner space 152 may be accessible via a proximal opening 153, such that the bone cement paste is introducible through the proximal opening 153 of the stem mold 151 into the inner space 152 and the metal core 160 can be partially pushed in through the proximal opening 153 into the inner space 152 of the stem mold 151. Around the proximal opening 153, the stem mold 151 may have a proximal wall 154 which delimits and encloses the proximal opening 153.

The head molds 155, 205 may have a hollow space 156, 206 in which the bone cement paste is shapeable to form a head 190 of the spacer 188. On a proximal side of the hollow space 156, 206, each of the hollow spaces 156, 206 may have a spherical surface-shaped inner surface 157, 207 which serves to form the actual joint surface of the spacer 188, 238. The spherical surface-shaped inner surfaces 157, 207 of the hollow spaces 156, 206 accordingly shape the hip joint surfaces of the spacer 188, 238, which are intended to slide in a hip socket.

The hollow spaces 156, 206 may be accessible via a distal opening 158, 208, such that the bone cement paste is introducible through the distal opening 158, 208 of the head molds 155, 205 into the hollow spaces 156, 206 and the metal core 160 can be partially pushed in through the distal openings 158, 208 into the hollow spaces 156, 206 of the head molds 155, 205. Around the distal opening 158, 208, the head molds 155, 205 may each have a distal wall 159, 209 which delimits and encloses the respective distal opening 158, 208.

Before being introduced, the bone cement paste may have been mixed from a monomer liquid and a cement powder (not shown), wherein at least one antibiotic and/or at least one antimycotic may preferably also be admixed with the bone cement paste. The bone cement paste can be filled into the stem mold 151 and into the head molds 155, 205 via a bone cement applicator 132, as shown in FIGS. 14 and 17 relating to the second exemplary embodiment.

The metal core 160 may consist of a biocompatible metal, such as for example stainless steel or titanium. The metal core 160 serves to reinforce and thus mechanically stabilize the spacer 188, 238. The metal core 160 has a stem part 162, a head part 164 and a flange 166, which is arranged between the stem part 162 and the head part 164. The metal core 160 is preferably one-part. The stem part 162 and the head part 164 may be connected together via the flange 166. The flange 166 may project out in the radial direction from the axes of the head part 164 and the stem part 162. The protruding flange 166 has a proximal surface 168 and an opposing distal surface 170.

The proximal wall 154 of the stem mold 151 may be shaped to match the distal surface 170 of the flange 166, such that the stem mold 151 is placeable at least in places flush against the distal surface 170 of the flange 166. This permits definite positioning of the stem mold 151 on the flange 166 of the metal core 160. Similarly, the distal wall 159, 209 of the head molds 155, 205 may be shaped to match the proximal surface 168 of the flange 166, such that the head molds 155, 205 are placeable at least in places flush against the proximal surface 168 of the flange 166. This permits definite positioning of the head molds 155, 205 on the flange 166 of the metal core 160.

A plurality of protruding spacing pieces 172 of an elongate shape may be arranged on the stem part 162, which spacing pieces facilitate positioning and orientation of the stem part 172 in the stem mold 151 when the stem part 162 is pushed through the proximal opening 153 into the stem mold 151. The height of the spacing pieces 172 is here selected such that they rest against the inner wall of the inner space 152 of the stem mold 151 when the stem part 162 is completely pushed into the stem mold 151. The limit stop for this purpose may be formed by the proximal wall 154 of the stem mold 151 and by the distal surface 170 of the flange 166.

A plurality of protruding centering means 174, for example in the form of four projecting fins, may be arranged on the head part 164, which centering means facilitate positioning and orientation of the head part 164 in the head molds 155, 205 when the head part 164 is pushed through the respective distal opening 158, 208. The orientation of the fins is preferably selected such that they can slide along the linear surfaces thereof into the hollow spaces 156, 206 of the head molds 155, 205. The head molds 155, 205 may have neck molds 178, 228 of different lengths with a cylindrical inner space as part of the hollow spaces 156, 206. The centering means 174 can slide on the cylindrical inner walls of the neck molds 178, 228. The height of the centering means 174 is preferably here selected such that they rest against the cylindrical inner walls of the hollow space 156, 206 of the neck molds 178, 228 when the head part 164 is completely pushed into the head molds 155, 205. The limit stop for this purpose may be formed by the distal walls 159, 209 of the head molds 155, 205 and by the proximal surface 168 of the flange 166.

The neck mold 178 may have a plurality of projecting rings 180 in the form of peripheral thickened portions along which the neck mold 178 can be cut and so shortened. The neck mold 228 may be understood as a maximally shortened neck mold 178. The rings 180 may be uniformly spaced, in particular in a uniform integral or half-integral centimeter or inch spacing. In this way, the length of a neck 194, 244 of the spacer 188, 238 to be produced, which is determined by the length of the respective neck mold 178, 228, can be adjusted.

The flange 166 may have a plurality of protrusions 182 which may project out in a radial or transverse direction from the metal core 166. The protrusions 182 may form the proximal surface 168 and/or the distal surface 170 of the flange 166 or be part of the proximal surface 168 and/or distal surface 170 of the flange 166. Excess bone cement paste may emerge from the stem mold 151 and theoretically also from the head molds 155, 205 between the interspaces between the projections 182 when the metal core 160 is pushed in.

A collar 184 may be formed on the stem mold 151, which collar, starting from the proximal wall 154 of the stem mold 151, surrounds the flange 166.

According to the invention, the stem mold 151 and the head molds 155, 205 can be inexpensively produced from plastics material by injection molding or can even also be produced from a thermoformed plastics film since, even during introduction of a high-viscosity bone cement paste, they do not have to withstand any very large forces. This is possible because according to the invention the bone cement paste is introduced into the stem mold 151 and the head molds 155, 205 as the casting mold without the metal core 160 already being arranged therein and consequently having to be flowed around. Arranging the metal core 160 in the stem mold 151 and in one of the head molds 155, 205 subsequent to the introduction of the bone cement paste is possible because the stem mold 151 and the head molds 155, 205 are placed against the flange 166 of the metal core 160 and can accordingly be arranged and oriented to fit with the metal core 160 and with one another. As a result, there is no need for the stem mold 151 and the head molds 155, 205 to be screwed or fastened together in a costly, pressure-absorbing and stable manner.

Figure 25:
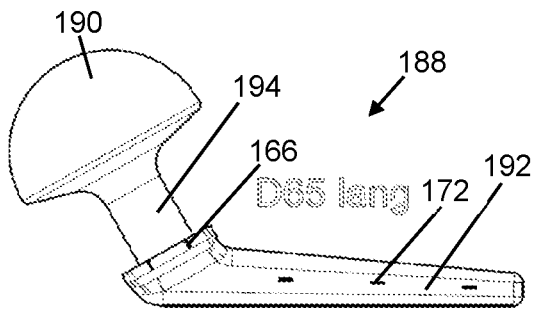
Figure 25:
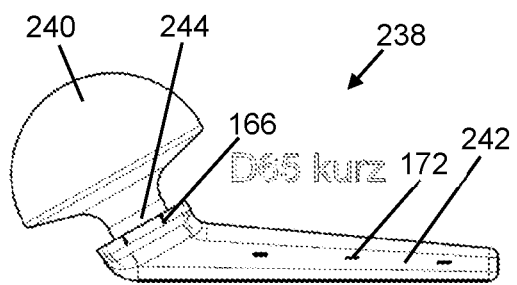
Figure 25:
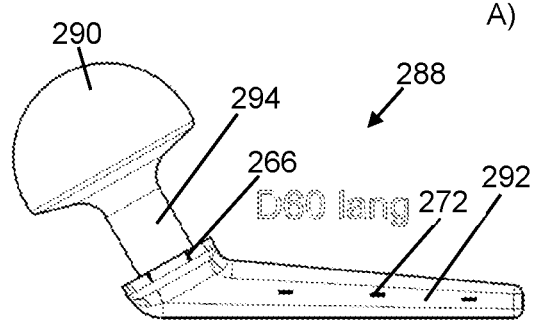
Figure 25:
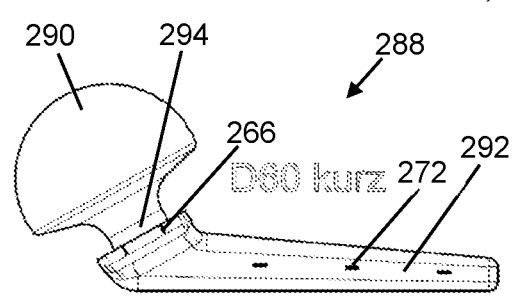
Figure 25:
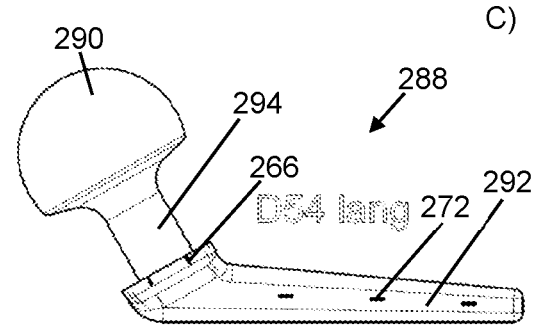
Figure 25:
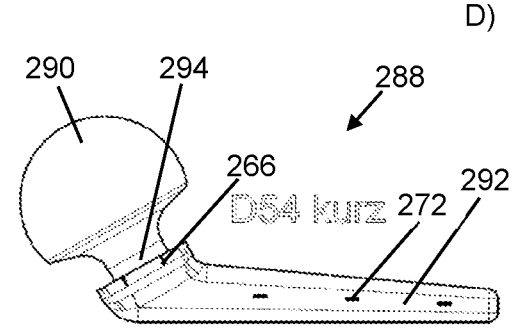
Figure 25:
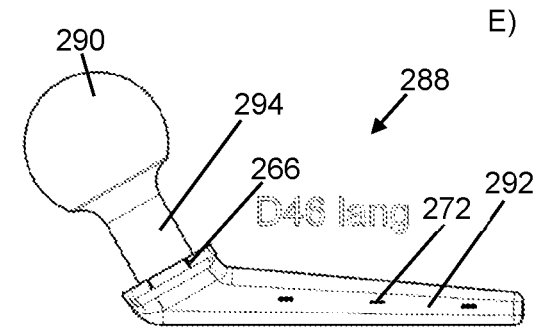
Figure 25:
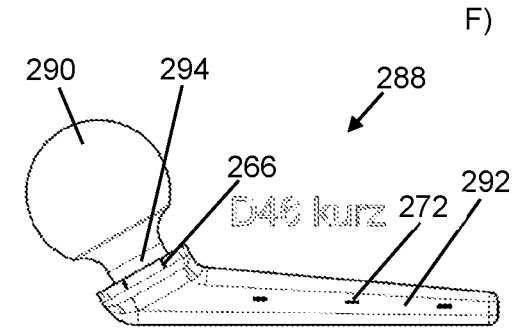

Once the bone cement paste in the casting mold assembled from the stem mold 151 and one of the head molds 155, 205 over the metal core 160 has cured, a bone cement paste contained therein may cure. The resultant spacer 188, 238 can subsequently be demolded by pulling off the stem mold 151 and separating and detaching the used head mold 155, 205. The spacer 188, 238, as shown in FIG. 25, is left behind, wherein the metal core 160 is enclosed or largely enclosed in the spacer 188, 238 as reinforcement. The flange 166 or the protrusions 182 of the flange 166 at the transition from the stem 192, 242 to the neck 294, 244 of the spacer 188, 238 are still apparent on the surface of the spacer 188, 238. The outer surfaces of the spacing pieces 172 in the stem 192, 242 and the centering means 174 in the neck 194, 244 of the spacer 188, 238 may likewise also be apparent.

The further variants, which are shown in FIGS. 24C) to 24H) and with which spacers 288 which can be produced in FIGS. 25C) to 25H) for a hip joint, are, apart from smaller diameters of the spherical surface-shaped inner surfaces 257, identical to those of the sets according to FIGS. 21 to 23 and 24A), 24B), 25A) and 25B). For simplicity's sake the same reference signs were used for all these exemplary embodiments, including those of different shapes.

The devices have a stem mold 251 and a head mold 255 and a metal core 260. The stem mold 251 and the head mold 255 are preferably in each case of one-part construction. The stem mold 251 and the head mold 255 may together form a two-part casting mold for shaping a bone cement paste introduced therein (not shown).

The stem mold 251 may have an inner space 252 in which the bone cement paste is shapeable to form a stem 292 of the spacer 288. The inner space 252 may be accessible via a proximal opening, such that the bone cement paste is introducible through the proximal opening of the stem mold 251 into the inner space 252 and the metal core 260 can be partially pushed in through the proximal opening into the inner space 252 of the stem mold 251. Around the proximal opening, the stem mold 251 may have a proximal wall which delimits and encloses the proximal opening.

The head mold 255 may have a hollow space 256 in which the bone cement paste is shapeable to form a head 290 of the spacer 288. On a proximal side of the hollow space 256, the hollow space 256 may have a spherical surface-shaped inner surface 257 of different diameters which serves to form the actual joint surface of the spacer 288. The spherical surface-shaped inner surface 257 of the hollow space 256 accordingly shapes the hip joint surface of the spacer 288, which surface is intended to slide in a hip socket. The hollow space 256 may be accessible via a distal opening, such that the bone cement paste is introducible through the distal opening of the head mold 255 into the hollow space 256 and the metal core 260 can be partially pushed in through the distal opening into the hollow space 256 of the head mold 255. Around the distal opening, the head mold 255 may have a distal wall which delimits and encloses the distal opening.

The metal core 160 may consist of a biocompatible metal, such as for example stainless steel or titanium. The metal core 160 serves to reinforce and thus mechanically stabilize the spacer 288. The metal core 260 has a stem part 262, a head part 264 and a flange 266, which is arranged between the stem part 262 and the head part 264. The metal core 260 is preferably one-part. The stem part 262 and the head part 264 may be connected together via the flange 266. The flange 266 may project out in the radial direction from the axes of the head part 264 and the stem part 262. The protruding flange 266 has a proximal surface and an opposing distal surface.

A plurality of protruding spacing pieces 272 of an elongate shape may be arranged on the stem part 262, which spacing pieces facilitate positioning and orientation of the stem part 262 in the stem mold 251 when the stem part 262 is pushed through the proximal opening into the stem mold 251. The height of the spacing pieces 272 is here selected such that they rest against the inner wall of the inner space 252 of the stem mold 251 when the stem part 262 is completely pushed into the stem mold 251.

A plurality of protruding centering means 274, for example in the form of four projecting fins, may be arranged on the head part 264, which centering means facilitate positioning and orientation of the head part 264 in the head mold 255 when the head part 264 is pushed through the distal opening into the head mold 255. The orientation of the fins is preferably selected such that they can slide along the linear surfaces thereof into the hollow space 256 of the head mold 255. The head mold 255 may have a neck mold 278 with a cylindrical inner space as part of the hollow space 256. The centering means 274 can slide on the inner wall of the neck mold 278. The height of the centering means 274 is preferably here selected such that they rest against the inner wall of the hollow space 256 of the neck mold 278 of the head mold 255 when the head part 264 is completely pushed into the head mold 255.

According to the invention, the stem mold 251 and the head mold 255 can be inexpensively produced from plastics material by injection molding or can even also be produced from a thermoformed plastics film since, even during introduction of a high-viscosity bone cement paste, they do not have to withstand any very large forces. This is possible because according to the invention the bone cement paste is introduced into the stem mold 251 and the head mold 255 as the casting mold without the metal core 260 already being arranged therein and consequently having to be flowed around. Arranging the metal core 260 in the stem mold 251 and in the head mold 255 subsequent to the introduction of the bone cement paste is possible because the stem mold 251 and the head mold 255 are placed against the flange 266 of the metal core 260 and can accordingly be arranged and oriented to fit with the metal core 260 and with one another. As a result, there is no need for the stem mold 251 and the head mold 255 to be screwed or fastened together in a costly, pressure-absorbing and stable manner.

Once the bone cement paste in the casting mold assembled from the stem mold 251 and the head mold 255 over the metal core 260 has cured, a bone cement paste contained therein may cure. The resultant spacer 288 can subsequently be demolded by pulling off the stem mold 251 and separating and detaching the head mold 255. The spacer 288, as shown in FIG. 25, is left behind, wherein the metal core 260 is enclosed or largely enclosed in the spacer 288 as reinforcement. The flange 266 at the transition from the stem 292 to the neck 294 of the spacer 288 is still apparent on the surface of the spacer 288. The outer surfaces of the spacing pieces 272 in the stem 292 and the centering means 274 in the neck 294 of the spacer 288 may likewise also be apparent.

The features of the invention disclosed in the preceding description, as well as in the claims, figures and exemplary embodiments, may be essential both individually and in any combination for realizing the invention in its various embodiments.

LIST OF REFERENCE SIGNS 1, 51, 151, 251 Stem mold
2, 52, 152, 252 Inner space
3, 53, 153 Proximal opening of the stem mold
4, 54, 154 Proximal wall of the stem mold
5, 55, 105, 155, 205, 255 Head mold
6, 56, 106, 156, 206, 256 Hollow space
7, 57, 107, 157, 207, 257 Spherical surface-shaped inner surface
8, 58, 108, 158 Distal opening of the head mold
9, 59, 109, 159 Distal wall of the head mold
10, 60, 160, 260 Metal core
12, 62, 162, 262 Stem part
14, 64, 164, 264 Head part
16, 66, 166, 266 Flange
18, 68, 168 Proximal surface of the flange
20, 70, 170 Distal surface of the flange
22, 72, 172, 272 Spacing piece
24, 74, 174, 274 Centering means
26, 76 Cone
28, 78, 128, 178, 228, 278 Neck mold
30, 80, 130, 180 Ring
32, 182 Protrusion
34, 84, 154 Collar
36, 86 Bone cement paste
38, 88, 188, 238, 288 Spacer
40, 90, 190, 240, 290 Head of the spacer
42, 92, 192, 242, 292 Stem of the spacer
44, 94, 194, 244, 294 Neck of the spacer
132 Bone cement applicator
134 Cartridge
136 Cartridge head
138 Vacuum port
140 Delivery tube
142 Sleeve nut

The invention claimed is:

1. A device for producing a spacer by curing bone cement paste, wherein the spacer is provided in the medical field for temporarily replacing a joint or part of a joint comprising an articulating surface of a head of the joint, the device having:
   a stem mold for shaping a stem of the spacer from bone cement paste, wherein the stem mold has in the interior thereof an inner space, wherein the inner space is accessible via a proximal opening on a proximal side of the stem mold and wherein the stem mold has a proximal wall which peripherally delimits the proximal opening of the stem mold,
   a head mold for shaping a head and a neck of the spacer from bone cement paste, wherein the head mold has in the interior thereof a hollow space, wherein the hollow space has a spherical surface-shaped inner surface for shaping a sliding surface of the head of the spacer and the hollow space is accessible via a distal opening on a distal side of the head mold, wherein the head mold has a distal wall which peripherally delimits the distal opening of the head mold,
   a metal core, wherein the metal core has a stem part, a head part and a flange, wherein the flange projects out from the metal core, wherein the flange is arranged between the stem part and the head part and wherein the flange has a proximal surface and a distal surface,
   wherein the stem mold and the stem part of the metal core are shaped such that the stem part is arranged in the inner space of the stem mold, when the proximal wall of the stem mold is resting against the distal surface of the flange,
   wherein the head mold and the head part of the metal core are shaped such that the head part is arranged in the hollow space of the head mold, when the distal wall of the head mold is resting against the proximal surface of the flange, and
   wherein the head mold has a neck mold for shaping a neck of the spacer, which neck connects the head and the stem, from bone cement paste, wherein the neck mold is tubular or hollow-cylindrical, wherein the distal opening and the distal wall of the head mold are both parts of the neck mold and the spherical surface-shaped inner surface of the hollow space is not part of the neck mold,
   wherein centering means are arranged on the head part to facilitate positioning and orientation of the head part in the head mold when the head part is pushed through the distal opening into the head mold,
   wherein the centering means rest against the inner wall of the hollow space of the neck mold of the head mold when the head part is completely pushed into the head mold,
   and, the head part is shaped on the proximal side thereof with a cone intended to facilitate its being pushed into the bone cement paste.

2. The device according to claim 1, characterized in that the metal core consists of the stem part, the head part and the flange and/or the metal core is one-part.

3. The device according to claim 1, characterized in that the stem mold and/or the head mold consists or consist of a plastics material, or of at least one plastics film or of an injection-molded plastics material.

4. The device according to claim 1, characterized in that the stem part is spaced in the inner space of the stem mold from inner walls of the stem mold which delimit the inner space, when the proximal wall of the stem mold is resting against the distal surface of the flange, or is resting flush against the distal surface of the flange.

5. The device according to claim 1, characterized in that the head part is spaced in the hollow space of the head mold from inner walls of the head mold which delimit the hollow space, when the distal wall of the head mold is resting against the proximal surface of the flange, or is resting flush against the proximal surface of the flange.

6. The device according to claim 1, characterized in that the head mold and the head part of the metal core are shaped such that the head part protrudes beyond the neck mold into the hollow space of the head mold, when the distal wall is resting against the proximal surface of the flange.

7. The device according to claim 1, characterized in that the length of the neck mold is adjustable by shortening the neck mold, wherein, predetermined cutting or tearing points are arranged on the neck mold and/or a scale is arranged externally on the neck mold.

8. The device according to claim 1, characterized in that the proximal surface of the flange limits displacement of the metal core in the head mold, or in the neck mold, and/or the distal surface of the flange limits displacement of the metal core in the stem mold.

9. The device according to claim 1, characterized in that centering means are arranged on the head part of the metal core, wherein the centering means project out from the surface of the head part, wherein the centering means space inner walls of the head mold from the head part, when the head part of the metal core is pushed into the hollow space of the head mold, or the neck mold of the head mold is spaced from the head part, when the head part of the metal core is pushed into the hollow space of the head mold.

10. The device according to claim 1, characterized in that spacing pieces are arranged on the stem part of the metal core, wherein the spacing pieces project out from the surface of the stem part, wherein the spacing pieces space inner walls of the stem mold from the stem part of the metal core, when the stem part of the metal core is pushed into the inner space of the stem mold.

11. The device according to claim 1, characterized in that the outer circumference of the flange is larger than at least one of the proximal opening of the stem mold and the distal opening of the head mold.

12. The device according to claim 1, characterized in that at least one vent opening is arranged in at least one of the stem mold and the head mold, wherein the at least one vent opening gas-permeably connects at least one of the inner space of the stem mold and the hollow space of the head mold with the surroundings of the device, wherein the at least one vent opening is permeable to gases and impermeable to bone cement paste.

13. The device according claim 1, characterized in that the device is intended to be used in a set with a cement powder packaged in at least one microbe-proof cement container and a monomer liquid packaged in at least one microbe-proof and liquid-tight monomer liquid container.

14. The device according to claim 13, characterized in that the device is intended to be used in a set with at least one bone cement cartridge for mixing the cement powder with the monomer liquid and for delivering mixed bone cement paste from the bone cement cartridge, wherein the at least one bone cement cartridge has the at least one microbe-proof cement container and contains the at least one microbe-proof and liquid-tight monomer liquid container, wherein the at least one microbe-proof cement container and the at least one microbe-proof and liquid-tight monomer liquid container are arranged in mutually separate regions.

15. A set for producing different spacers by curing bone cement paste, wherein the spacers are provided in the medical field for temporarily replacing a joint or part of a joint comprising an articulating surface of a head of the joint, the set having at least one device according to claim 1, wherein the set has at least two head molds with different diameters of the spherical surface-shaped inner surfaces and/or at least two stem molds with hollow spaces of different lengths in the distal direction or different internal diameters of the hollow spaces.

16. The set according to claim 15, characterized in that the set has at least two metal cores with a different length of the head part and/or stem part.

17. A method for producing a spacer for temporarily replacing a joint or part of a joint, or a hip joint or a shoulder joint, comprising an articulating surface of the joint, wherein the method is carried out with the device according to claim 1 or with a set for producing different spacers by curing bone cement paste, wherein the spacers are provided in the medical field for temporarily replacing a joint or part of a joint comprising an articulating surface of a head of the joint, the set having at least one device according to claim 1, wherein the set has at least two head molds with different diameters of the spherical surface-shaped inner surfaces and/or at least two stem molds with hollow spaces of different lengths in the distal direction or different internal diameters of the hollow spaces, the method having the following steps:
  A) introducing a bone cement paste into the inner space of the stem mold and introducing a bone cement paste into the hollow space of the head mold;
  B) pushing the head part of the metal core into the hollow space, filled with bone cement paste, of the head mold, so displacing the bone cement paste contained therein, until the distal wall of the head mold is resting against the proximal surface of the flange of the metal core, and pushing the stem part of the metal core into the inner space, filled with bone cement paste, of the stem mold, so displacing the bone cement paste contained therein, until the proximal wall of the stem mold is resting against the distal surface of the flange of the metal core;
  C) curing the bone cement paste in the head mold and the stem mold; and
  D) removing the resultant shaped and cured spacer from the head mold and the stem mold.

18. The method according to claim 17, characterized in that, before step A), a neck mold of the head mold is shortened in accordance with a desired length of the neck of the spacer to be produced, a head mold with a matching internal diameter of the spherical surface-shaped inner surface is selected to match the desired shape of the head of the spacer to be produced, a stem mold with an inner space matching the desired shape of the stem of the spacer to be produced is selected and/or a metal core with dimensions matching the desired shape of the stem of the spacer to be produced is selected.

19. The method according to claim 17, characterized in that, before step A), the homogeneous bone cement paste is produced by mixing a monomer liquid and a cement powder, wherein in step A) the mixed bone cement paste is pressed with a bone cement cartridge into the inner space of the stem mold and into the hollow space of the head mold, wherein in so doing the air is expelled from the inner space of the stem mold and from the hollow space of the head mold.

20. The method according to claim 17, characterized in that, in step B), the head part of the metal core is centered in the head mold with the assistance of centering means, or with the assistance of centering fins, which project out from the surface of the head part and which, when the head part is pushed into the hollow space of the head mold, rest against inner walls of the hollow space of the head mold.

21. The method according to claim 17, characterized in that, in step B), the stem part of the metal core is centered in the stem mold with the assistance of spacing pieces, which project out from the surface of the stem part and which, when the stem part is pushed into the inner space of the stem mold, rest against inner walls of the inner space of the stem mold.

* * * * *